(12) United States Patent
Jones et al.

(10) Patent No.: US 11,752,042 B2
(45) Date of Patent: *Sep. 12, 2023

(54) ABSORBENT ARTICLES WITH CURVED ELASTICIZED LAMINATES

(71) Applicant: Kimberly-Clark Worldwide, Inc., Neenah, WI (US)

(72) Inventors: Matthew R. Jones, Appleton, WI (US); James R. Niedt, Grand Chute, WI (US); Robert W. Scholl, Sherwood, WI (US); Kirk J. Dempsey, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,416

(22) Filed: Oct. 5, 2022

(65) Prior Publication Data

US 2023/0026804 A1 Jan. 26, 2023

Related U.S. Application Data

(63) Continuation of application No. 17/419,388, filed as application No. PCT/US2018/068148 on Dec. 31, 2018, now Pat. No. 11,497,655.

(51) Int. Cl.
*A61F 13/15* (2006.01)
*A61F 13/49* (2006.01)
(Continued)

(52) U.S. Cl.
CPC .. *A61F 13/15593* (2013.01); *A61F 13/15609* (2013.01); *A61F 13/15699* (2013.01);
(Continued)

(58) Field of Classification Search
None
See application file for complete search history.

(56) References Cited

U.S. PATENT DOCUMENTS

| 4,917,746 A | 4/1990 | Kons et al. |
| 5,525,175 A | 6/1996 | Blenke et al. |

(Continued)

FOREIGN PATENT DOCUMENTS

| CN | 1085494 A | 4/1994 |
| CN | 1711059 A | 12/2005 |

(Continued)

*Primary Examiner* — Barbara J Musser
(74) *Attorney, Agent, or Firm* — KIMBERLY-CLARK WORLDWIDE, INC.

(57) ABSTRACT

Absorbent articles having curved elasticized laminates and apparatuses and methods for forming such articles are disclosed. In one embodiment a method of forming an article may comprise moving absorbent assemblies and elasticized laminates in the machine direction. The method may further comprise oscillating the elasticized laminates in the cross-machine direction to impart a curvature, bonding the elasticized laminates to the absorbent assemblies while maintaining the imparted curvature such that at least a portion of the elasticized laminates are disposed outboard of longitudinal side edges of the absorbent assemblies, and finally separating the absorbent assemblies into individual absorbent articles, where the elasticized laminates extend in a curving manner throughout the absorbent articles.

20 Claims, 18 Drawing Sheets

(51) Int. Cl.
*A61F 13/494* (2006.01)
*A61F 13/496* (2006.01)

(52) U.S. Cl.
CPC ........ *A61F 13/4902* (2013.01); *A61F 13/496* (2013.01); *A61F 13/49017* (2013.01); *A61F 13/4942* (2013.01); *A61F 13/49413* (2013.01)

(56) References Cited

U.S. PATENT DOCUMENTS

| | | | |
|---|---|---|---|
| 5,827,387 | A | 10/1998 | Reynolds et al. |
| 5,911,713 | A | 6/1999 | Yamada et al. |
| 5,993,433 | A | 11/1999 | St. Louis et al. |
| 4,704,116 | B1 | 10/2000 | Enloe |
| 6,284,081 | B1 | 9/2001 | Vogt et al. |
| 6,287,409 | B1 | 9/2001 | Stephany |
| 6,589,149 | B1 | 7/2003 | VanEperen et al. |
| 7,731,815 | B2 | 6/2010 | Eckstein et al. |
| 8,062,454 | B2 | 11/2011 | Yamamoto et al. |
| 8,257,535 | B2 | 9/2012 | Yamamoto |
| 8,764,926 | B2 | 7/2014 | Bäck |
| 8,858,749 | B2 | 10/2014 | Ogasawara et al. |
| 8,944,129 | B2 | 2/2015 | Yamamoto |
| 2003/0083636 | A1 | 5/2003 | Kuen et al. |
| 2003/0120248 | A1 | 6/2003 | Miyamoto |
| 2006/0122571 | A1 | 6/2006 | Chang et al. |
| 2010/0193139 | A1 | 8/2010 | Eckstein et al. |
| 2016/0270973 | A1 | 9/2016 | Surushe et al. |
| 2017/0216105 | A1 | 8/2017 | Bäck et al. |

FOREIGN PATENT DOCUMENTS

| | | |
|---|---|---|
| CN | 104812346 A | 7/2015 |
| CN | 107708638 A | 2/2018 |
| EP | 2522323 B1 | 6/2017 |
| RU | 94018227 A | 3/1996 |
| WO | 2000007534 A1 | 2/2000 |
| WO | 2016159983 A1 | 10/2016 |
| WO | 2018160156 A1 | 9/2018 |

ABSORBENT ARTICLES WITH CURVED ELASTICIZED LAMINATES

This is a continuation of U.S. application Ser. No. 17/419,388, filed Jun. 29, 2021, now U.S. Pat. No. 11,497,655.

TECHNICAL FIELD

The present disclosure relates to absorbent articles, and more specifically to absorbent articles having curved elasticized webs.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

One common mode of failure is for exudates to leak past containment flaps and out of the leg openings of an absorbent article. As one example, fecal material that is not absorbed or contained by the absorbent article can move over or through any containment features disposed proximate the leg cuffs of the articles and soil or contaminate the wearer's skin and clothing near their legs. This may be more common of an occurrence for semi-solid fecal material, such as low viscosity fecal material, which can be prevalent with younger children. Such exudates can move around on the bodyside liner of an absorbent article under the influence of gravity, motion, and pressure by the wearer of the absorbent article. In such a circumstance, not only does the wearer's absorbent article need to be changed, but the wearer's clothing and/or bedding often also needs to be changed, resulting in additional work, expense, and stress for the caregiver.

Attempts have been made in the past to provide containment systems, especially on the bodyside liner or near the leg cuffs to solve the problems described above. Some examples involve utilizing elasticized containment flaps and/or leg cuffs, having various different structures, to provide better gasketing around a wearer's body and legs to help prevent leakage. Although such containment flaps and leg cuffs have helped to reduce the amount and frequency of leaking, failures still occur. Thus, there is a desire for improvements to absorbent articles to prevent leakage of exudates.

SUMMARY OF THE DISCLOSURE

The present disclosure relates to absorbent articles, and more specifically to absorbent articles having curved elasticized webs.

In one embodiment, a method of forming an absorbent article may comprise moving a stream of connected absorbent assemblies in a machine direction, the absorbent assemblies comprising: a bodyside liner, an outer cover, and an absorbent body disposed between the bodyside liner and the outer cover, the absorbent body having a length in the machine direction that is greater than a width in a cross-machine direction. The method may further comprise moving a first pair of elasticized laminates in the machine direction, each of the first pair of elasticized laminates comprising: a laminate material comprising a fold to form a laminate material top layer and a laminate material bottom layer, and an elastomeric member disposed between the laminate material top layer and the laminate material bottom layer. The method may still further comprise oscillating, with a laminate oscillating device, each of the first pair of elasticized laminates in the cross-machine direction to impart a curvature to each of the first pair of elasticized laminates, bonding each of the first pair of elasticized laminates to the stream of connected absorbent assemblies while maintaining the imparted curvature such that at least a portion of the fold of each of the first pair of elasticized laminates is disposed outboard of longitudinal side edges of the stream of connected absorbent assemblies, and separating the stream of connected absorbent assemblies into individual absorbent articles, each article comprising a front region, a rear region, and a crotch region disposed between the front region and the rear region, wherein the fold and the elastomeric member of each elasticized laminate of each individual absorbent article extend in a curving manner throughout at least the crotch region of each individual absorbent article.

In another embodiment, a method of forming an absorbent article may comprise moving a stream of connected absorbent assemblies in a machine direction, the absorbent assemblies comprising: a bodyside liner, an outer cover, and an absorbent body disposed between the bodyside liner and the outer cover, the absorbent body having a length in the machine direction that is greater than a width in a cross-machine direction. The method may further comprise moving a first pair of elasticized laminates in the machine direction, each of the first pair of elasticized laminates comprising: a laminate material having first side edge and a second side edge, at least one of the first side edge and the second side edge being a folded edge, wherein the laminate material comprises a laminate material top layer and a laminate material bottom layer; and an elastomeric member disposed between the laminate material top layer and the laminate material bottom layer. The method may still further comprise oscillating, with a laminate oscillating device, each of the first pair of elasticized laminates in the cross-machine direction to impart a curvature to each of the first and second side edges of each of the first pair of elasticized laminates, bonding each of the first pair of elasticized laminates to the stream of connected absorbent assemblies while maintaining the imparted curvature, and separating the stream of connected absorbent assemblies into individual absorbent articles, each article comprising a front region, a rear region, and a crotch region disposed between the front region and the rear region, wherein the first and second side edges and the elastomeric member of each elasticized laminate of each individual absorbent article extend in a curving manner throughout at least the crotch region of each individual absorbent article.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which.

Figure 1:
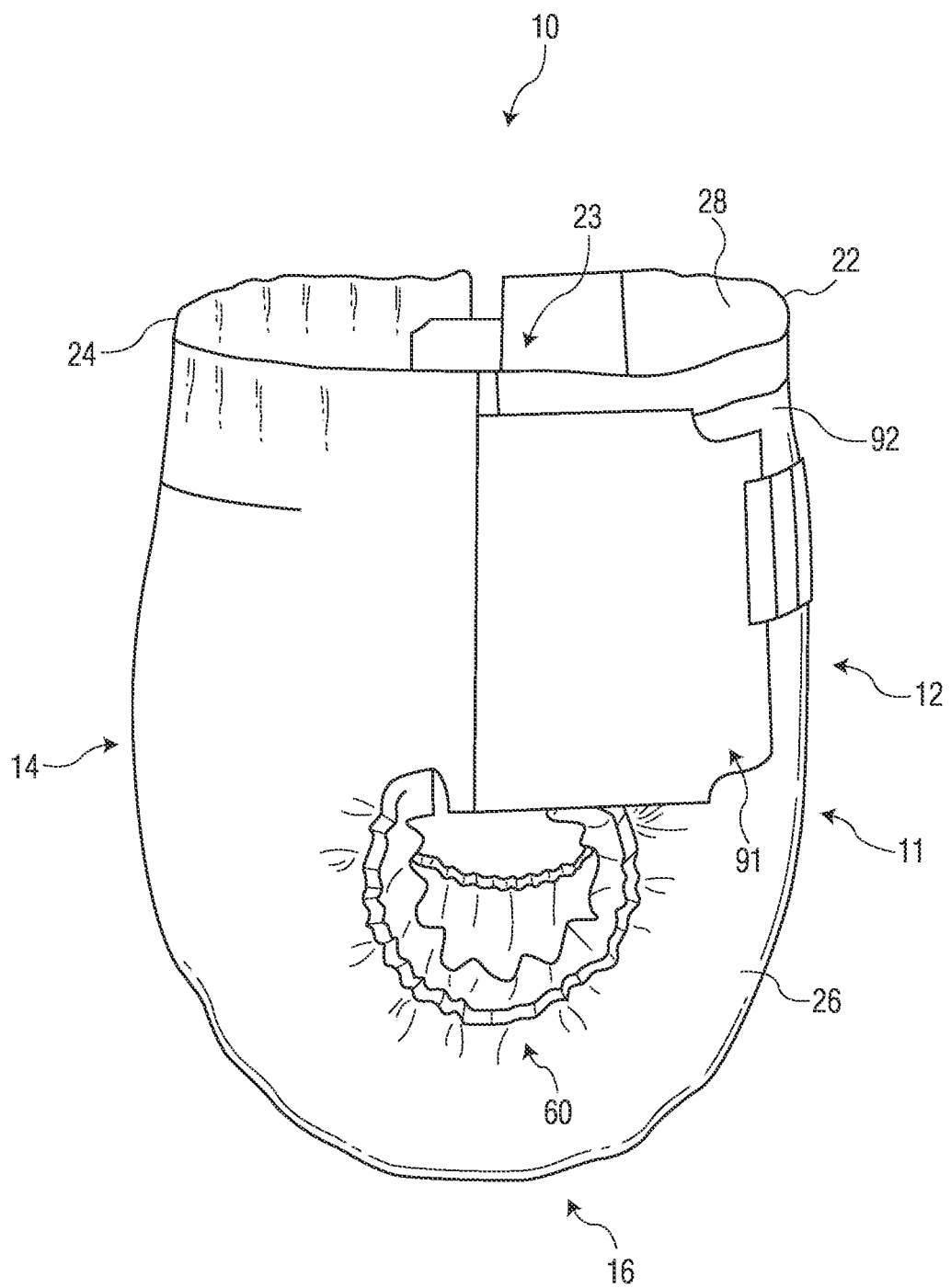
FIG. 1 is side perspective view of an exemplary embodiment of an absorbent article according to aspects of the present disclosure, such as a diaper, in a fastened condition.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The present disclosure is generally directed toward absorbent articles having curved elasticized webs for use as containment flaps and/or leg cuffs. Such curved elasticized webs may allow for better gasketing of the wearer's body and/or legs, which helps to retain bodily exudates within the absorbent article. For example, curved leg cuffs may allow for a better, more uniform fit of the absorbent article on a wearer, allowing for better gasketing of the wearer's body by the article. Curved elasticized containment flaps may allow for non-uniform coverage of a wearer's body by the containment flaps, thereby strategically allowing for larger openings around common bodily fluid insult locations while also allowing for strategically placed smaller openings, which provide for greater body coverage by the article. Such strategically located greater body coverage helps to reduce skin exposure to the bodily exudates, which in turn can help to reduce incidents of skin irritation from contact between the wearer's body and the exudates.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article:

Referring to FIGS. 1-15, non-limiting illustrations of an exemplary absorbent articles 10, 110, 210, 310, and 410 for example, a diaper, are illustrated. Although, the articles 10, 110, 210, 310, and 410 may be a training pant, youth pant, adult incontinence garment, or feminine hygiene article in other embodiments. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent articles 10, 110, 210, 310, and 410 illustrated in FIGS. 1-15 can include a chassis 11. The absorbent articles 10, 110, 210, 310, and 410 can further include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region.

The absorbent articles 10, 110, 210, 310, and 410 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length. In other embodiments, such as the one shown in FIG. 2, the longitudinal side edges 18, 20 can be curved between the front waist edge 22 and the rear waist edge 24.

The front waist region 12 can include the portion of the absorbent articles 10, 110, 210, 310, and 410 that, when worn, is positioned at least in part on the front of the wearer while the rear waist region 14 can include the portion of the absorbent articles 10, 110, 210, 310, and 410 that, when worn, is positioned at least in part on the back of the wearer. The crotch region 16 of the absorbent articles 10, 110, 210, 310, and 410 can include the portion of the absorbent articles 10, 110, 210, 310, and 410 that, when worn, is positioned between the legs of the wearer and can partially cover the lower torso of the wearer. The waist edges, 22 and 24, of the absorbent articles 10, 110, 210, 310, and 410 are configured to encircle the waist of the wearer and together define a central waist opening 23 (as labeled in FIG. 1) for the waist of the wearer. Portions of the longitudinal side edges 18, 20 in the crotch region 16 can generally define leg openings for the legs of the wearer when the absorbent articles 10, 110, 210, 310, and 410 is worn.

The absorbent articles 10, 110, 210, 310, and 410 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which can coincide with the length and width of the absorbent articles 10, 110, 210, 310, and 410, but is not necessary in all embodiments. The absorbent articles 10, 110, 210, 310, and 410 can have a longitudinal axis 29 extending in the longitudinal direction 30 and a lateral axis 31 extending in the lateral direction 32.

The chassis 11 can include an absorbent body 34. The absorbent body 34 can be disposed between the outer cover 26 and the bodyside liner 28, as depicted for example in FIG. 3. The absorbent body 34 can have longitudinal edges, 36 and 38, which, in an embodiment, can form portions of the longitudinal side edges, 18 and 20, respectively, of the absorbent articles 10, 110, 210, 310, and 410. The absorbent body 34 can have a first end edge 40 that is opposite a second end edge 42, respectively, which, in an embodiment, can form portions of the waist edges, 22 and 24, respectively, of the absorbent articles 10, 110, 210, 310, and 410. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent articles 10, 110, 210, 310, and 410. The bodyside liner 28, the outer cover 26, and the absorbent body 34 can form part of an absorbent assembly 44. The absorbent assembly 44 can also include a fluid transfer layer (not shown) and a fluid acquisition layer (not shown) between the bodyside liner 28 and the fluid transfer layer as is known in the art. The absorbent assembly 44 can also include a spacer layer (not shown) disposed between the absorbent body 34 and the outer cover 26.

The absorbent articles 10, 110, 210, 310, and 410 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent articles 10, 110, 210, 310, and 410 can suitably include a waist containment member (not shown). In some embodiments, the waist containment member can be disposed in the rear waist region 14 of the absorbent articles 10, 110, 210, 310, and 410. It is contemplated that the waist containment member can be additionally or alternatively disposed in the front waist region 12 of the absorbent articles 10, 110, 210, 310, and 410. In some embodiments, the waist containment member may be formed and incorporated into any of the embodiments described herein according to any of the waist containment members and articles described in U.S. Patent Application Publication No. 2018/0055698, titled "Absorbent article with selectively positioned waist containment member" to Bishop et al. and assigned to Kimberly-Clark Worldwide Inc. or U.S. Patent Application Publication No. 2017/0246054, titled "Absorbent article with absorbent body providing improved access to containment pocket of waist containment member" to Bishop et al. and assigned to Kimberly-Clark Worldwide Inc., both of which are hereby incorporated herein in their entirety.

The absorbent articles 10, 110, 210, 310, and 410 can further include elasticized leg cuffs 62. The elasticized leg cuffs 62 may generally comprise one or more elastomeric members 63, such as elastomeric ribbons or strands. These elastomeric members 63 can be attached to the outer cover 26 and/or the bodyside liner 28 along the opposite longitudinal side edges, 18 and 20, in some embodiments and are generally positioned in the crotch region 16 of the absorbent articles 10, 110, 210, 310, and 410. In some embodiments, the elasticized leg cuffs 62 extend in a generally parallel direction to the longitudinal axis 29, as shown for example in FIG. 4. In other embodiments, however, the elasticized leg cuffs 62 can be curved, as shown for example in FIG. 2.

Additional details regarding each of these elements of the absorbent articles 10, 110, 210, 310, and 410 described herein can be found below and with reference to the FIGS. 1-15.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

Figure 3:
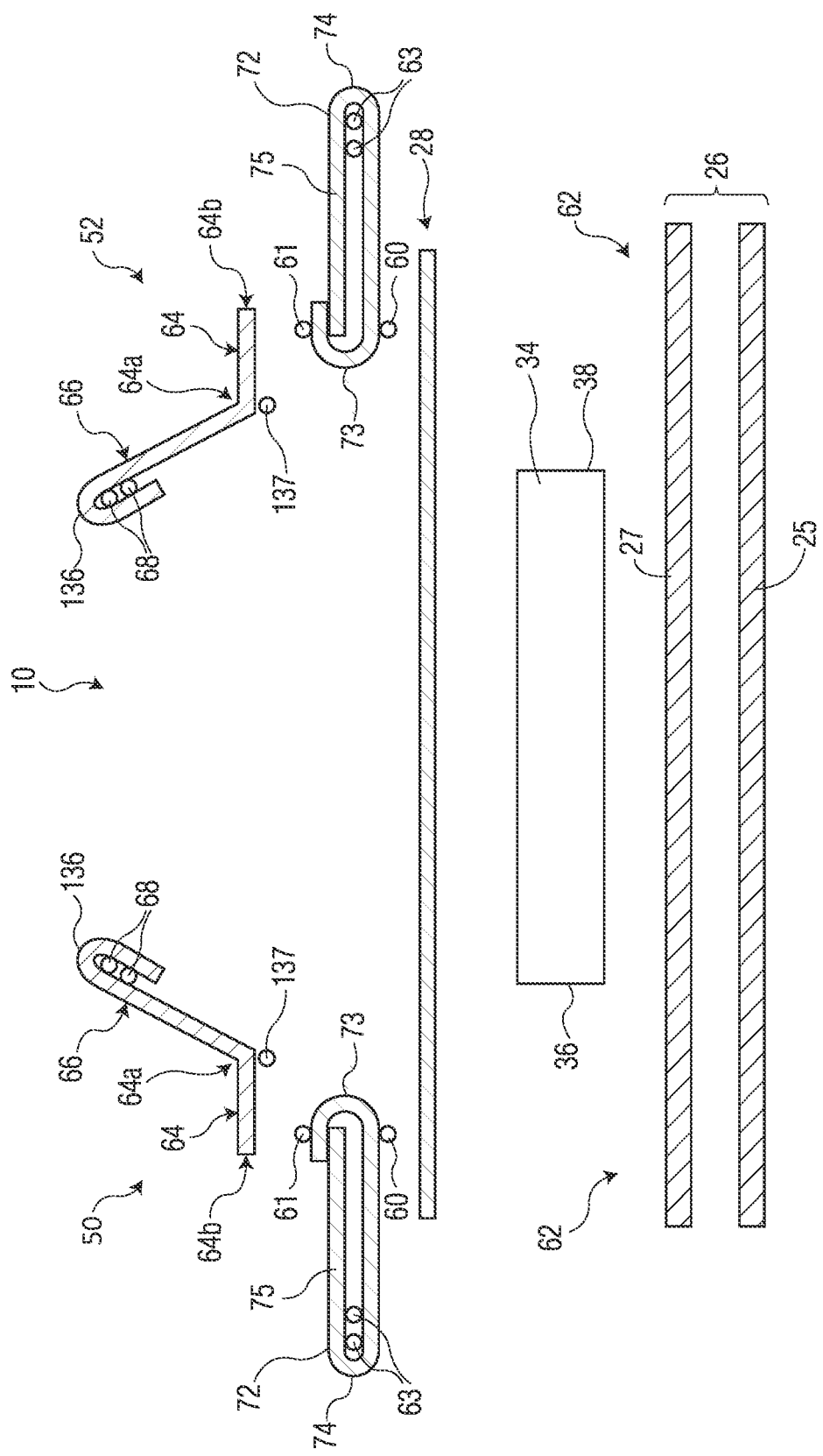
FIG. 3 is a cross-sectional view taken along line 3-3 of the article of FIG. 2.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent articles 10, 110, 210, 310, and 410. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. For example, the outer cover 26 can be a two-layer construction, including a softer outer layer 25 and an inner, liquid impermeable layer 27, as shown in FIG. 3, which can be bonded together such as by a laminate adhesive (not shown). Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent articles 10, 110, 210, 310, and 410 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent articles 10, 110, 210, 310, and 410 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent articles 10, 110, 210, 310, and 410. The absorbent body 34 can have a length and width that can be less than or equal to the length and width of the absorbent article 10, 110, 210, 310, and 410.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

If a spacer layer (not shown) is present, the absorbent body 34 can be disposed on the spacer layer and superposed over the outer cover 26. The spacer layer can be bonded to the outer cover 26, for example, by adhesive. In some embodiments, a spacer layer may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer (not shown) and/or a spacer layer, can be positioned between the absorbent body 34 and the outer cover 26. The absorbent body 34 can be bonded to the fluid transfer layer and/or the spacer layer.

Bodyside Liner:

The bodyside liner 28 of the absorbent articles 10, 110, 210, 310, and 410 can overlay the absorbent body 34 and the outer cover 26 and can isolate the wearer's skin from liquid waste retained by the absorbent body 34. In various embodiments, a fluid transfer (not shown) layer can be positioned between the bodyside liner 28 and the absorbent body 34. In various embodiments, an acquisition layer (not shown) can be positioned between the bodyside liner 28 and the absorbent body 34 or a fluid transfer layer, if present. In various embodiments, the bodyside liner 28 can be bonded to the acquisition layer, or to the fluid transfer layer if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer, if present, and/or an acquisition layer, if present, and/or a spacer layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. It is contemplated that the bodyside liner 28 may be narrower than the outer cover 26. However, in other embodiments, the bodyside liner 28 and the outer cover 26 may be of the same dimensions in width and length. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Pat. No. 9,474,660 to by Kirby et al., the entirety of which is incorporated herein in its entirety.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent articles 10, 110, 210, 310, and 410. In other aspects, the bodyside liner 28 can be stretchable, and more suitably elastic, in both the lateral and the longitudinal directions 32, 30, respectively.

Fastening System:

In an embodiment, the absorbent articles 10, 110, 210, 310, and 410 can include a fastening system. The fastening system can include one or more back fasteners 91 and one or more front fasteners 92. The embodiment being shown in FIG. 1 depict an embodiment with one front fastener 92. Portions of the fastening system may be included in the front waist region 12, rear waist region 14, or both.

The fastening system can be configured to secure the absorbent articles 10, 110, 210, 310, and 410 about the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2.

Figure 2:
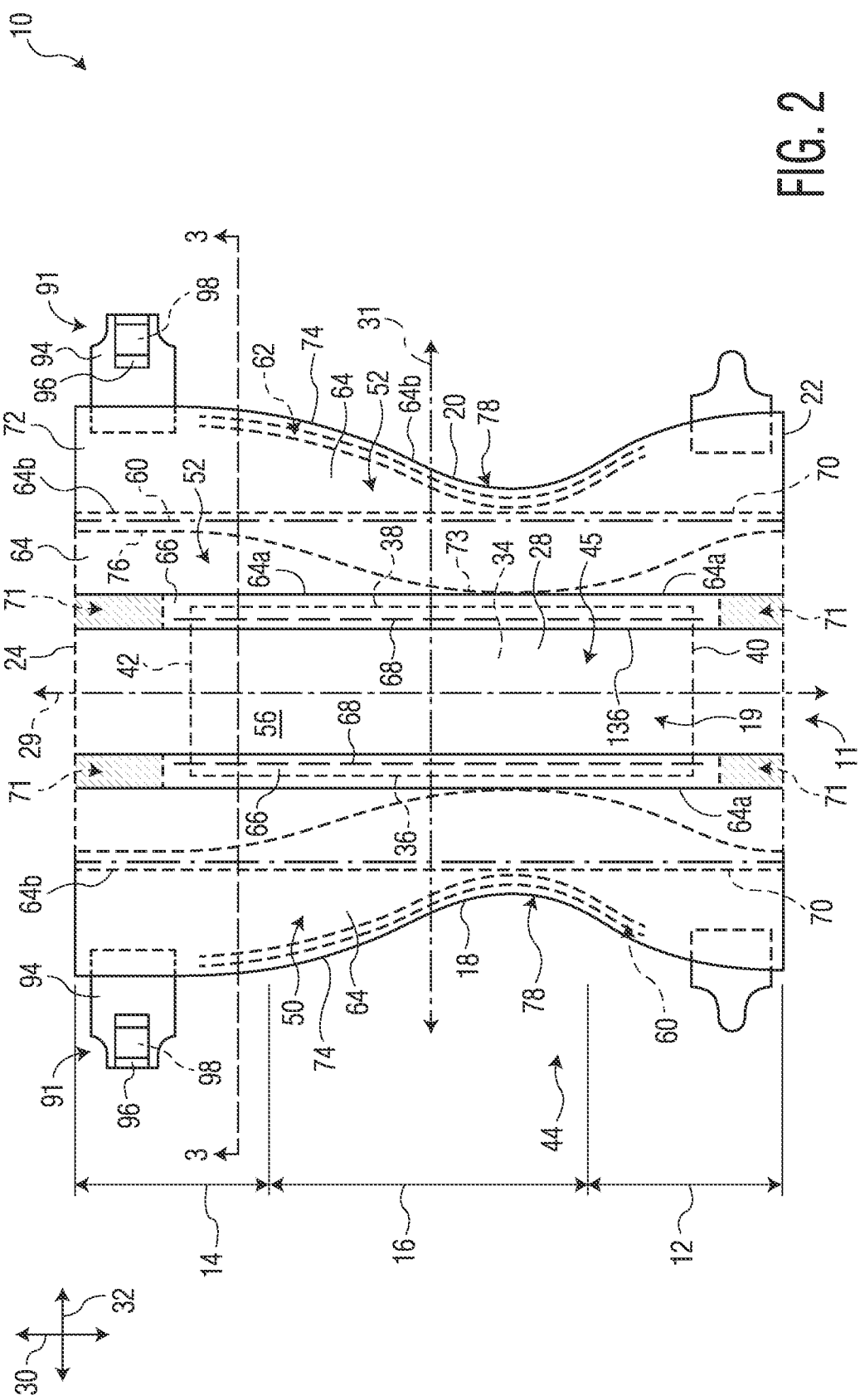
FIG. 2 is an exemplary top plan view of an embodiment of the absorbent article of FIG. 1 in a stretched, laid flat, unfastened condition.

Leg Cuffs:

FIGS. 2 and 3 depict an exemplary absorbent article 10 according to aspects of the present disclosure where the article 10 comprises curved elasticized leg cuffs 62. FIG. 2 depicts exemplary absorbent article 10 in a laid-flat, stretched configuration while FIG. 3 is a cross-section of the article 10 of FIG. 2 as viewed along line 3-3. Providing the elasticized leg cuffs 62 with such curvature can help to achieve a better fit around a wearer's body. For example, such inward curvature of the leg cuffs 62 as shown in FIG. 2 aligns better with the anatomy of a wearer than an article comprising straight leg cuffs 62 in that the crotch region 16 of article 10 is generally intended to be disposed between the narrow region between a wearer's legs. Providing such curvature also provides a cue to the wearer about proper positioning of the article 10 when worn. Both of these factors can help to reduce leakage incidents by ensuring that proper gasketing of the wearer is achieved by the leg cuffs 62 and by the containment flaps 50, 52.

In the embodiment of FIGS. 2 and 3, the elasticized leg cuffs 62 may be formed separately from the article chassis 11 and subsequently attached to the article chassis 11 to form the elasticized leg cuffs 62, as opposed to being formed integrally with the chassis 11 such as by being positioned between the outer cover 26 and the bodyside liner 28 or between separate layers of the outer cover 26 or the like. In such embodiments, the elasticized leg cuffs 62 may each comprise an elasticized laminate 72 formed from a leg cuff material 75 with one or more elastomeric members 63 disposed between the leg cuff material 75. The leg cuff material 75 can be folded over to sandwich the members 63 between a top layer of the leg cuff material 75 and a bottom layer of the leg cuff material 75, as shown in FIG. 3, producing folded edges 73, 74. Alternatively, the leg cuff material 75 may comprise two separate pieces, which are bonded together with the members 63 disposed therebetween to form the laminates 72. The elastomeric members 63 are secured through adhesive and/or mechanical bonds such as those formed by heat, pressure, and/or ultrasonic energy, as known in the art. Although not explicitly shown, the material 75 may be bonded together at locations other than proximate the elastomeric members 68 as needed to maintain the integrity of the laminates 72. For example, where the material 75 comprises a single, folded piece of material, at least the ends of the material 75 may be bonded to the material 75 so there are no loose ends hanging off the laminates 72. In general, the elasticized laminates 72 may be formed such that the laminates 72 have a uniform width along their length—although this is not required in all embodiments.

The elasticized laminates 72 may be attached to the chassis 11 along bonds 60 such that the elasticized laminates 72 have a laminate outer edge 74 and a laminate inner edge 73. Although shown as straight bonds 60 in FIG. 2, in other embodiments it is contemplated that the bonds 60 may be curved, for example to match the curvature of the elasticized laminates 72. In some embodiments the bonds 60 may comprise a single adhesive bead, while in other embodiments the bonds 60 may comprise multiple adhesive beads, or sprayed, swirled, or slot coated adhesive or even mechanical bonds. The bonds 60 may even cover the entire extent of the laminates 72 which are disposed over the body-facing surface 45 of the absorbent assembly 44.

Just prior to attachment to the chassis 11, the elasticized laminates 72 may be oscillated back and forth to impart a curve to the laminates 72. The imparted curve is then maintained as the laminates 72 are attached to the chassis 11 through bond 60 in this curved manner. As can be seen in FIG. 2, the laminate outer edge 74 and the laminate inner edge 73 extend along the length of the article 10 in a curving manner. The process to impart the curvature and attach the laminates 72 to the chassis 11 is described in more detail below.

As can be seen in FIG. 2, when the laminates 72 are bonded to the chassis 11, the outer edges 74 of the elasticized laminates 72 may extend outboard beyond the outer edges 70 of the chassis 11. That is, the outer edges 74 of the elasticized laminates 72 may be disposed further away from the longitudinal axis 29 of the article 10 than the outer edges 70 of the chassis 11. In some contemplated embodiments, at least the laminate outer edges 74 may be folded edges, as shown in FIG. 3. In this manner, the longitudinal side edges 18, 20 of the overall article 10 may comprise the outer edges 74 of the laminates 72, providing clean, non-frayed or frilled edges to the article 10. Such a configuration is appealing to consumers and can provide a functional benefit in some article designs. For example, many articles having a curved chassis are formed from a straight chassis with portions of the chassis cut off to give a curvature to the chassis. This cutting results in frayed or frilled edges which can be quite long in some instances. In particular designs, these frayed or frilled edges can fold inward over the chassis and bridge containment flaps 50, 52 of such articles, thereby disrupting the gasketing function of the flaps 50, 52 which can result in leakage. The design of the articles 10 of the present disclosure also have the advantage of allowing formation of an absorbent article with curved side edges without forming waste material by forming the curved shape through material cut-outs.

In the embodiment of FIGS. 2 and 3, the elastomeric members 63 of the elasticized leg cuffs 62 are disposed completely laterally outboard of the outer edges 70 of the chassis 11. Although, in other embodiments, at least portions of the elastomeric members 63 may overlap the chassis 11.

In these embodiments where the elasticized leg cuffs 62 are curved, the apex 78 of the curvature of the cuffs 62 may be disposed at different locations along the length of the article 10 in different embodiments. The apex 78 of the curvature is defined as the locations along the outer edges 74 of the elasticized laminates 72 which are closest to the longitudinal axis 29. In some embodiments, the apex 78 is disposed in the front waist region 12, while in other embodiments, the apex 78 is disposed in the crotch-region 16. Wherein the apex 78 is disposed in the crotch region, the apex 78 may be disposed within the front half of the article 10. That is, the apex 78 may be disposed closer to the front waist edge 22 of the article 10 than the lateral axis 31. Although, in alternative contemplated embodiments, the apex 78 may be disposed in the rear waist region 14 or in the rear half of the article 10.

In some particular embodiments, the curvature of the laminates 72 may be such that the apex 78 may be closer to the longitudinal axis 29 than the location along the outer edges 74 of the laminates 72 which are furthest from the longitudinal axis 29 by between about 10% and about 40% of the distance between the location along the outer edges 74 of the laminates 72 which are furthest from the longitudinal axis 29 and the longitudinal axis 29. For example, if the location along the outer edges 74 of the laminates 72 which are furthest from the longitudinal axis 29 are disposed 110 mm away from the longitudinal axis 29, the apex 78 may be between about 99 mm and about 66 mm away from the longitudinal axis 29. In further embodiments, the apex 78 may be closer by between about 15% and about 35% or between about 20% and about 30%.

Containment Flaps:

The absorbent article 10 can further include a pair of containment flaps 50, 52. In general, one containment flap 50 can be disposed on a first side of the longitudinal axis 29 and the other containment flap 52 can be disposed on a second side of the longitudinal axis 29. In an embodiment, the containment flaps 50, 52 can extend generally in a longitudinal direction 30 from the front waist region 12 of the absorbent article 10 through the crotch region 16 to the rear waist region 14 of the absorbent article 10.

In some embodiments the containment flaps 50, 52 can be formed separately from the absorbent chassis 11 and attached to the chassis 11 or can be formed integral to the chassis 11. The containment flaps 50, 52 can be secured to the chassis 11 of the absorbent article 10 in a generally parallel, spaced relation with each other laterally inward of the leg openings to provide a barrier against the flow of body exudates, as shown with respect to the embodiments of FIGS. 2 and 3. In alternative embodiments, such as some of the embodiments described with respect to FIGS. 4-6, the containment flaps may be curved along their length.

Where the article includes containment flaps 50, 52, the flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64a and a distal end 64b. The projection portion 66 can be separated from the base portion 64 at the proximal end 64a of the base portion 64. As used in this context, the projection portion 66 is separated from the base portion 64 at the proximal end 64a of the base portion 64 in that the proximal end 64a of the base portion 64 defines a transition between the projection portion 66 and the base portion 64. The proximal end 64a of the base portion 64 can be located near the barrier adhesive 137 (as shown in FIG. 3). In some embodiments, the distal ends 64b of the base portion 64 can laterally extend to the respective longitudinal side edges 70 of the chassis 11. In other embodiments, the distal ends 64b of the base portion 64 can end laterally inward of the respective longitudinal side edges 70 of the chassis 11. The containment flaps 50, 52 can also each include a projection portion 66 that is configured to extend away from the body facing surface 19 of the chassis 11 at least in the crotch region 16 when the absorbent article 10 is in a relaxed configuration. The containment flaps 50, 52 can include a tack-down region 71 in either or both of the front waist region 12 and the rear waist region 14 where the projection portion 66 is coupled to the body facing surface 19 of the chassis 11.

The containment flaps 50, 52 can include one or more flap elastic members 68, such as the two flap elastic strands depicted in FIG. 3. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIGS. 2 and 3, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, when the absorbent article 10 is in a relaxed configuration.

In some embodiments, the containment flaps 50, 52 can be bonded to the chassis 11 after the elasticized laminates 72 are bonded to the chassis, thereby placing the elasticized laminates 72 between the flaps 50, 52 and the body-side liner 28 as shown in FIG. 3. In such embodiments, the laminates 72 may be bonded to the containment flaps 50, 52 at least through bond 61. The bond 61 may be an adhesive bead, or may comprise multiple adhesive beads, or sprayed, swirled, or slot coated adhesive or any type of mechanical bond.

According to some embodiments of the present disclosure, the laminates 72 may be disposed beneath the flaps 50, 52, and the laminate inner edges 73 may be disposed wholly outboard of the proximal end portions 64a of the containment flaps 50, 52 such that the barrier adhesive 137 bonds the flaps 50, 52 directly to the body-facing surface 19 of the chassis 11, such as to the body-side liner 28. According to some designs, the bonding between the containment flaps 50, 52 and the body-facing surface 19 may represent a liquid-impermeable bond such that bodily exudates cannot wick or leak beyond (e.g. outboard) the proximal end portions 64a of the flaps 50, 52. In these designs, it is important for the laminate inner edges 73 to be disposed outboard of the proximal end portions 64a (and thus, outboard of the barrier adhesive 137) so as not to interfere with this liquid-impermeable barrier created by the barrier adhesive 137 bonding the proximal end portions 64a of the flaps 50, 52 to the body-facing surface 19 of the chassis 11. In other embodiments, however, at least a portion of the laminate inner edges 73 may extend inboard of the barrier adhesive 137. In such embodiments, the laminate material 75 may be a hydrophobic material which does not wick fluid (or may be made hydrophobic through application of one or more hydrophobic coatings). In alternative embodiments, adhesive may be strategically disposed between and throughout the laminate material 75 in sufficient quantity to form a liquid-impermeable barrier within the laminates 72, thereby forming a liquid-impermeable barrier between the laminates 72 and the body facing surface 19 of the chassis and between the laminates 72 and the containment flaps 50, 52.

In some alternative embodiments, the laminates 72 may be disposed on top of the containment flaps 50, 52. In such embodiments, the containment flaps 50, 52 may be bonded directly to the body-facing surface 19 of the chassis 11 by the barrier adhesive 137, forming a liquid impermeable barrier. In these embodiments, the laminate inner edges 73 may not extend inboard of the proximal end portions 64a of the flaps so as not to interfere with any lifting of the projection portions 66 during use so that the projection portions 66 may properly gasket the wearer's body to prevent leakage. In other embodiments, the laminate inner edges 73 may extend inboard of the proximal end portions 64a as long as the bond 60 is disposed outboard of the proximal end portions 64a and wherein the laminate inner edges 73 do not extend inward further than the projection portion distal ends 136, when the article 10 is in a laid-flat, stretched configuration.

Figure 4:
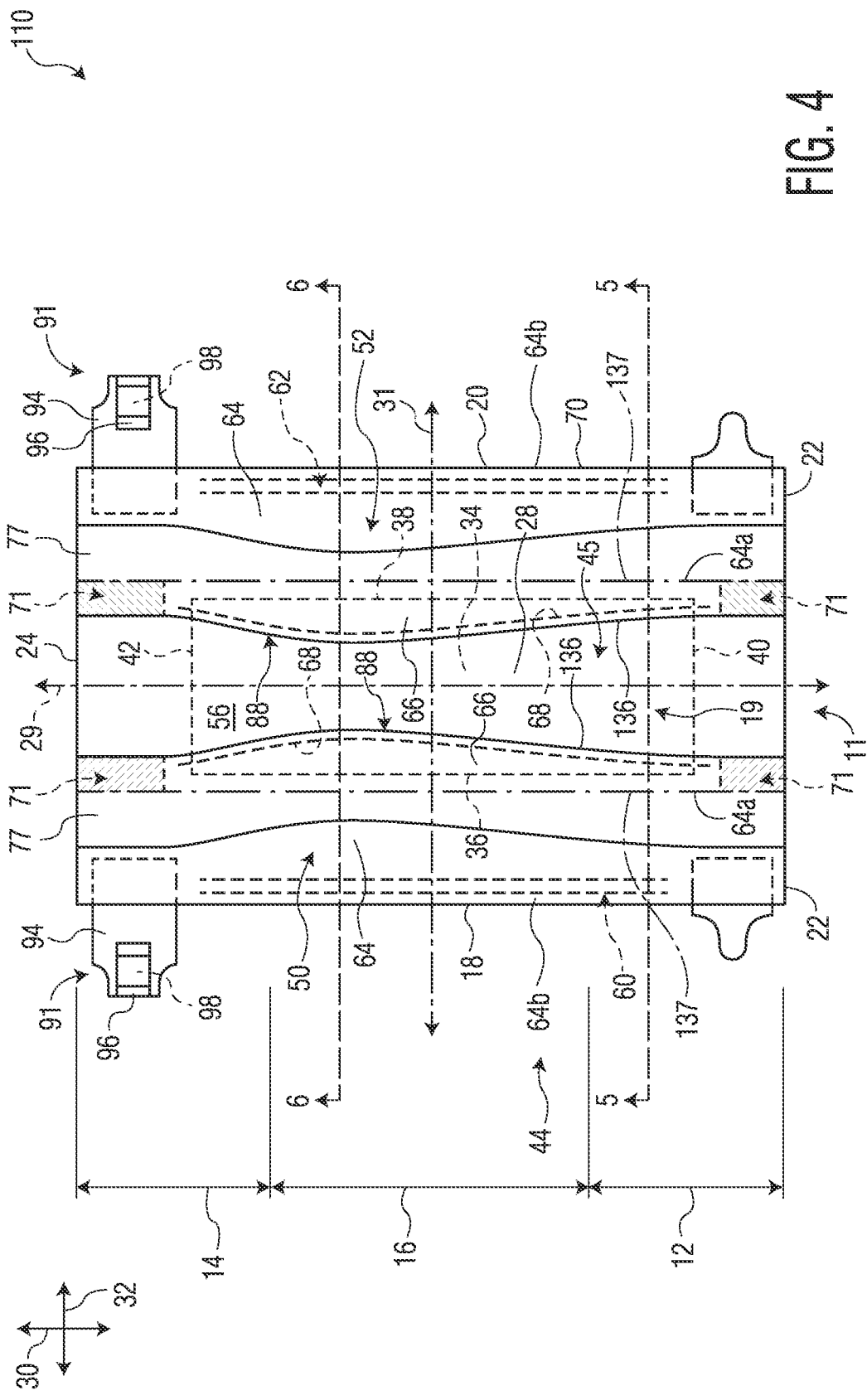
FIG. 4 is an exemplary top plan view of another embodiment of an absorbent article according to aspects of the present disclosure, in a stretched, laid flat, unfastened condition.
Figure 5:
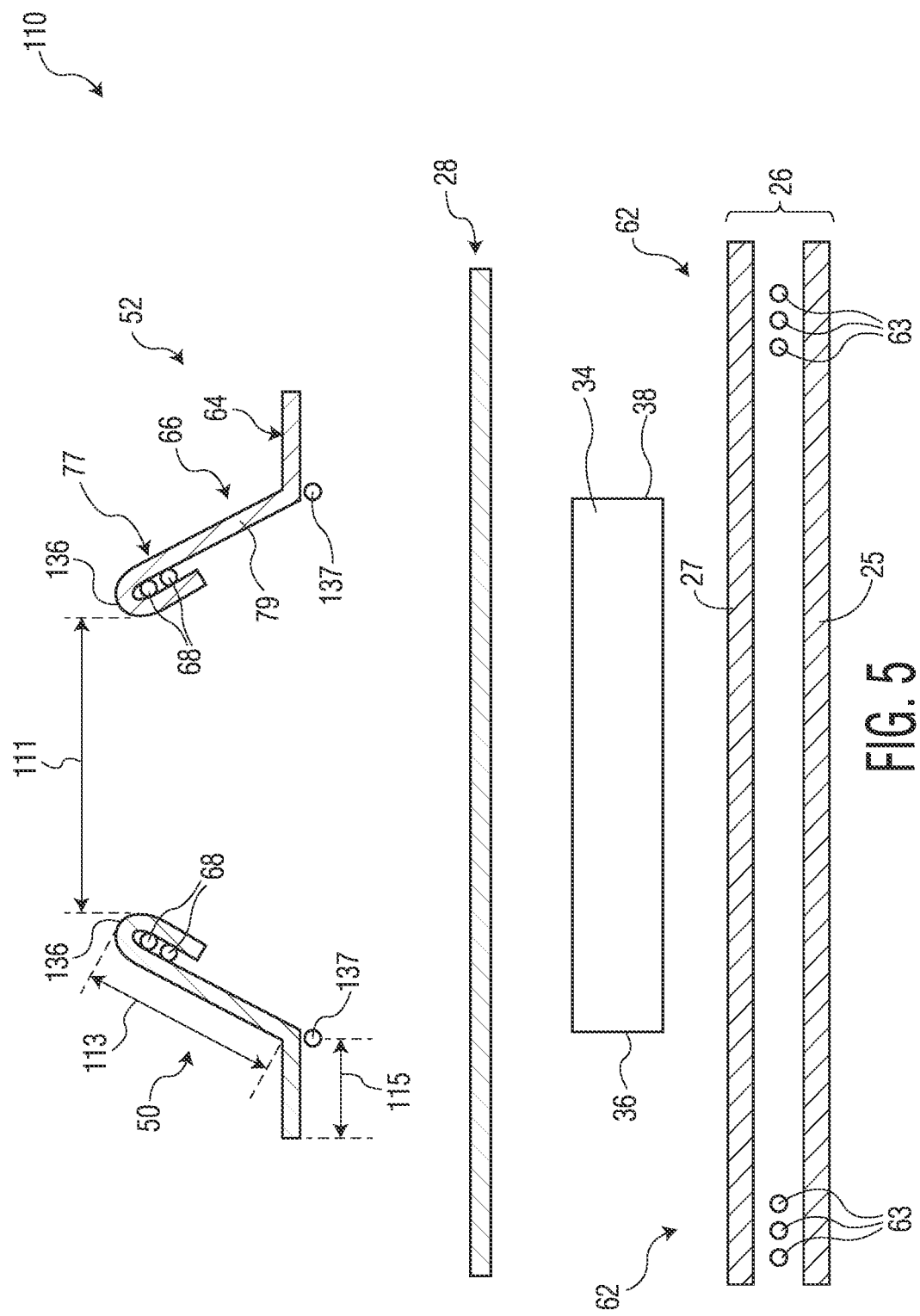
FIG. 5 is a cross-sectional view taken along line 5-5 of the article of FIG. 4.
Figure 6:
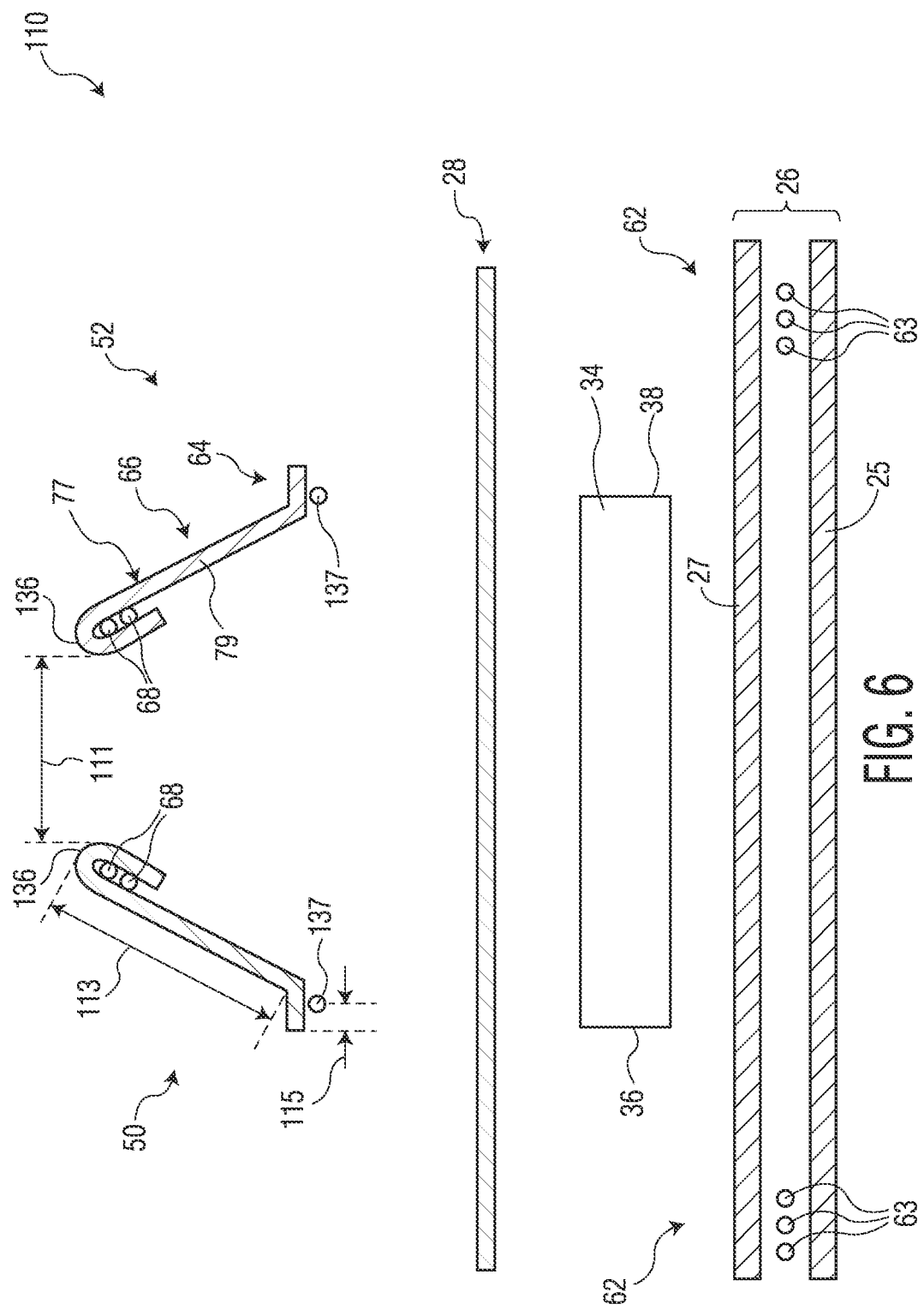
FIG. 6 is a cross-sectional view taken along line 6-6 of the article of FIG. 4.

FIGS. 4-6 depict an exemplary embodiment of an absorbent article 110 according to the present disclosure. FIG. 4 depicts the exemplary article 110 in a laid-flat, stretched configuration while the FIGS. 5 and 6 depict cross sections of the article 110 of FIG. 4 as viewed along lines 5-5 and 6-6, respectively. More specifically, the embodiment of FIGS. 4-6 represents an absorbent article 110 having curved containment flaps 50, 52. Curving the containment flaps 50, 52, according to aspects of the present disclosure, may allow for greater overall coverage of the body-facing surface 45 of the absorbent assembly 44 by the flaps 50, 52, or at least greater coverage of the body-facing surface 45 where bodily exudates tend to locate or pool after insult. More specifically, the curvature of the containment flaps 50, 52 produces a narrower opening between the projection portions 66 of the flaps 50, 52 proximate the location of the inward curvature of the flaps 50, 52, thereby leaving less wearer skin exposed to the body-facing surface 45 near the narrowed opening. Because skin exposure to bodily exudates remaining on the body-facing surface 45 is one of the leading causes of skin irritation, it is generally beneficial to reduce the amount of skin exposed to such bodily exudates.

In the embodiment of FIGS. 4-6, the leg cuffs 62 may be formed integrally with the chassis 11. For example, the elastomeric members 63 of the cuffs 62 may be disposed between the outer cover 26 and the body-side liner 28 or between separate layers of the outer cover 26 or the like. These embodiments contrast with the embodiments of FIGS. 2 and 3 where the leg cuffs 62 were formed by attaching elasticized laminates 72 formed separately from the chassis 11 to the chassis 11.

The containment flaps 50, 52 of FIGS. 4-6, similar to the leg cuffs 62 of the embodiments in FIGS. 2 and 3, may be formed from elasticized laminates 77 formed separately from the chassis 11 and attached thereto to form the flaps 50, 52. The elasticized laminates 77 are formed from a containment flap material 79 with one or more elastomeric members 68 disposed between the containment flap material 79. At least a portion of the containment flap material 79 can be folded over to sandwich the members 68 between a top layer of the containment flap material 79 and a bottom layer of the containment flap material 79, as shown in FIGS. 5 and 6. In other embodiments, the material 79 may be folded such that ends of the material 79 overlap, similar to the elastic laminate 72 as shown in FIG. 3. Alternatively, the containment flap material 79 may comprise two separate pieces, which are bonded together with the members 68 disposed therebetween to form the laminates 77. In general, the elasticized laminates 77 may be formed such that the laminates 77 have a uniform width along their length—although this is not required in all embodiments. The elastomeric members 68 are secured through adhesive and/or mechanical bonds. Although not explicitly shown, the material 79 may be bonded together at locations other than proximate the elastomeric members 68 as needed to maintain the integrity of the laminates 77.

The elasticized laminates 77 may be attached to the chassis 11 along barrier adhesives 137 to form the containment flaps 50, 52. In the embodiments of FIGS. 4-6, the laminates 77 may be oscillated back and forth to impart a curvature just prior to the laminates 77 being attached to the chassis 11. In this manner, the curvature of the laminates 77 is maintained through attachment of the laminates to the chassis 11 by the barrier adhesive 137. In some embodiments, the portions of the laminates 77 outboard of the barrier adhesive 137, as shown in FIG. 4, may be bonded to the chassis 11 so as to not allow any free edge portions of the laminates 77. Such bonding may be accomplished by having a wide barrier adhesive 137 which covers the portions of the laminates 77 which are disposed outboard of the proximal end portions 64a. In other embodiments, a separate adhesive region may extend along the base portion distal ends 64b. For example, an adhesive bead may be curved to match the curvature of the base portion distal ends 64b to secure at least the base portion distal ends 64b to the chassis 11.

In the embodiment of FIGS. 4-6, the barrier adhesives 137 are applied to the chassis 11 in a straight line while the laminates 77 are applied to the chassis 11 in a curved manner. These features impart the containment flaps 50, 52 with a varying flap height 113. The flap height 113 is defined as the length of the projection portions 66, e.g. the distance between the proximal end portions 64a and the projection portion distal ends 136. This varying flap height 113 provides the article with varying projection portion spacing 111, as can be seen through comparison of the projection portion spacing 111 between the FIGS. 5 and 6. This varying projection portion spacing 111 helps to shield relatively more of a wearer's skin from bodily exudates that are present on the body-facing surface 45 of the absorbent assembly 44, which can result in reduced skin irritation.

According to some aspects of the present disclosure, the smallest projection portion spacing 111 may be between about 15% and about 40% of the largest projection portion spacing 111. For example, if the largest projection portion spacing 111 is 80 mm, then the smallest projection portion spacing 111 may be between about 12 mm and about 32 mm. In further embodiments, the smallest projection portion spacing 111 may be between about 20% and about 35% of the largest projection portion spacing 111, or between about 20% and about 30% in other embodiments. It has been found that these ranges strike a good balance of allowing higher coverage of a wearer's skin while maintaining a large enough opening so that bodily exudates flow from the wearer between the projection portions 66 and onto the body-facing surface 45 instead of flowing from the wearer to on-top of the containment flaps 50, 52 which will produce leaking.

It has been found that useful flap heights 113 for forming the desired projection portion spacing 111 are where the smallest flap height 113 is between about 25% and about 55% of the largest flap height 113. For example, if the largest flap height is 50 mm, then the smallest flap height 113 may be between about 12.5 mm and about 27.5 mm. In further embodiments, the smallest flap height 113 may be between about 30% and about 50% of the largest flap height 113, or between about 35% and about 45% in other embodiments. Because the laminates 77 are pre-formed and attached the chassis 11, the length 115 of the proximal portions 64 will change correspondingly as the flap height 113 changes.

In these embodiments where the containment flaps 50, 52 are curved, the apex 88 of the curvature of the flaps 50, 52 may be disposed at different locations along the length of the article 110 in different embodiments. The apex 88 of the curvature is defined as the locations along the projection portion distal ends 136 of the elasticized laminates 77 which are closest to the longitudinal axis 29. In some embodiments, the apex 88 is disposed in the rear waist region 14, while in other embodiments, the apex 88 is disposed in the crotch-region 16. Wherein the apex 88 is disposed in the crotch region, the apex 88 may be disposed within the rear half of the article 110. That is, the apex 88 may be disposed closer to the rear waist edge 24 of the article 110 than the lateral axis 31. This positioning may allow for greater coverage of a wearer's skin where fecal material is typically located in such articles 110—fecal material being a stronger skin irritant than urine. Of course, in alternative contemplated embodiments, the apex 88 may be disposed in the front waist region 12 or in the front half of the article 110.

Figure 7:
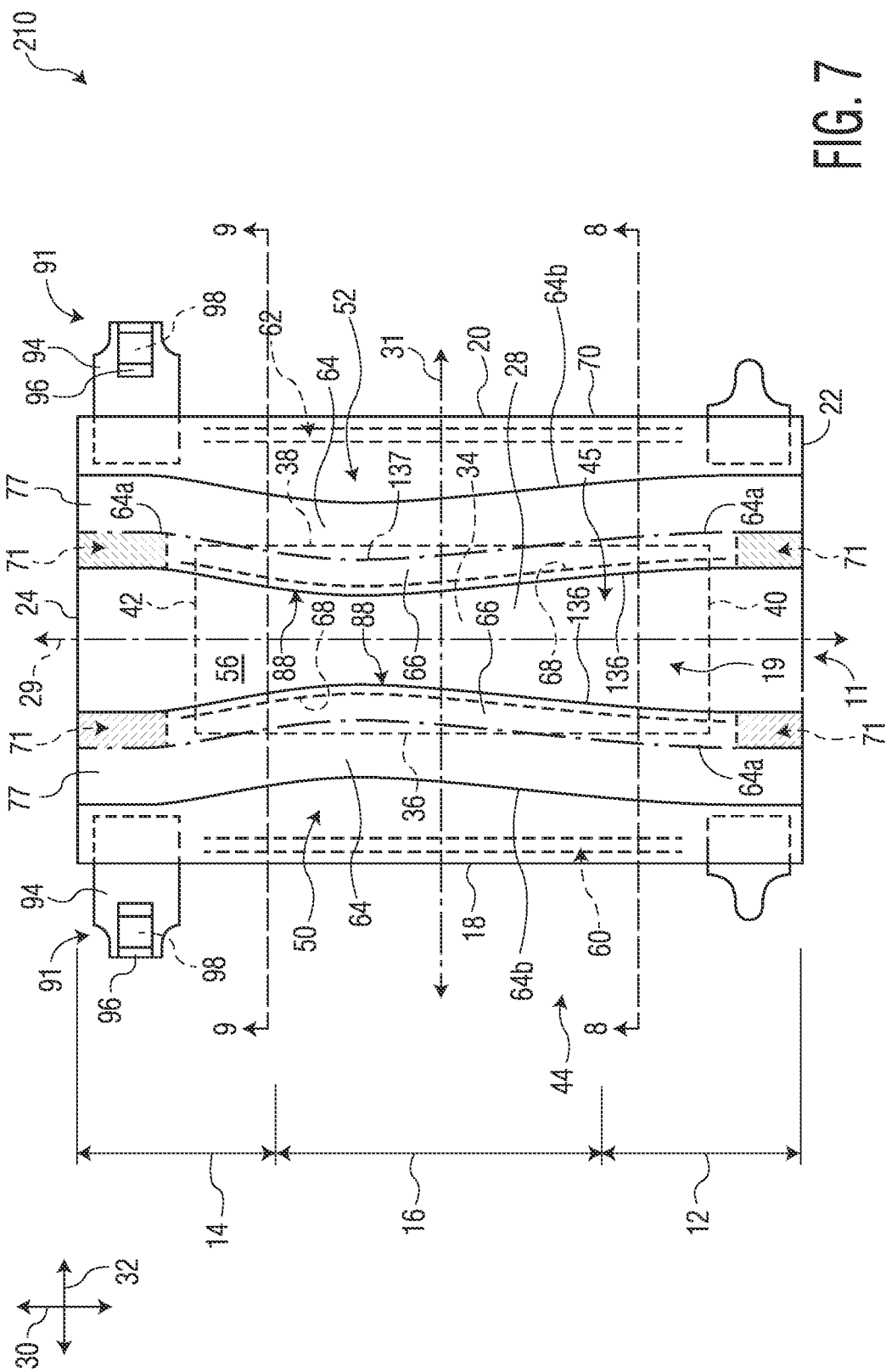
FIG. 7 is an exemplary top plan view of another embodiment of an absorbent article according to aspects of the present disclosure, in a stretched, laid flat, unfastened condition.
Figure 8:
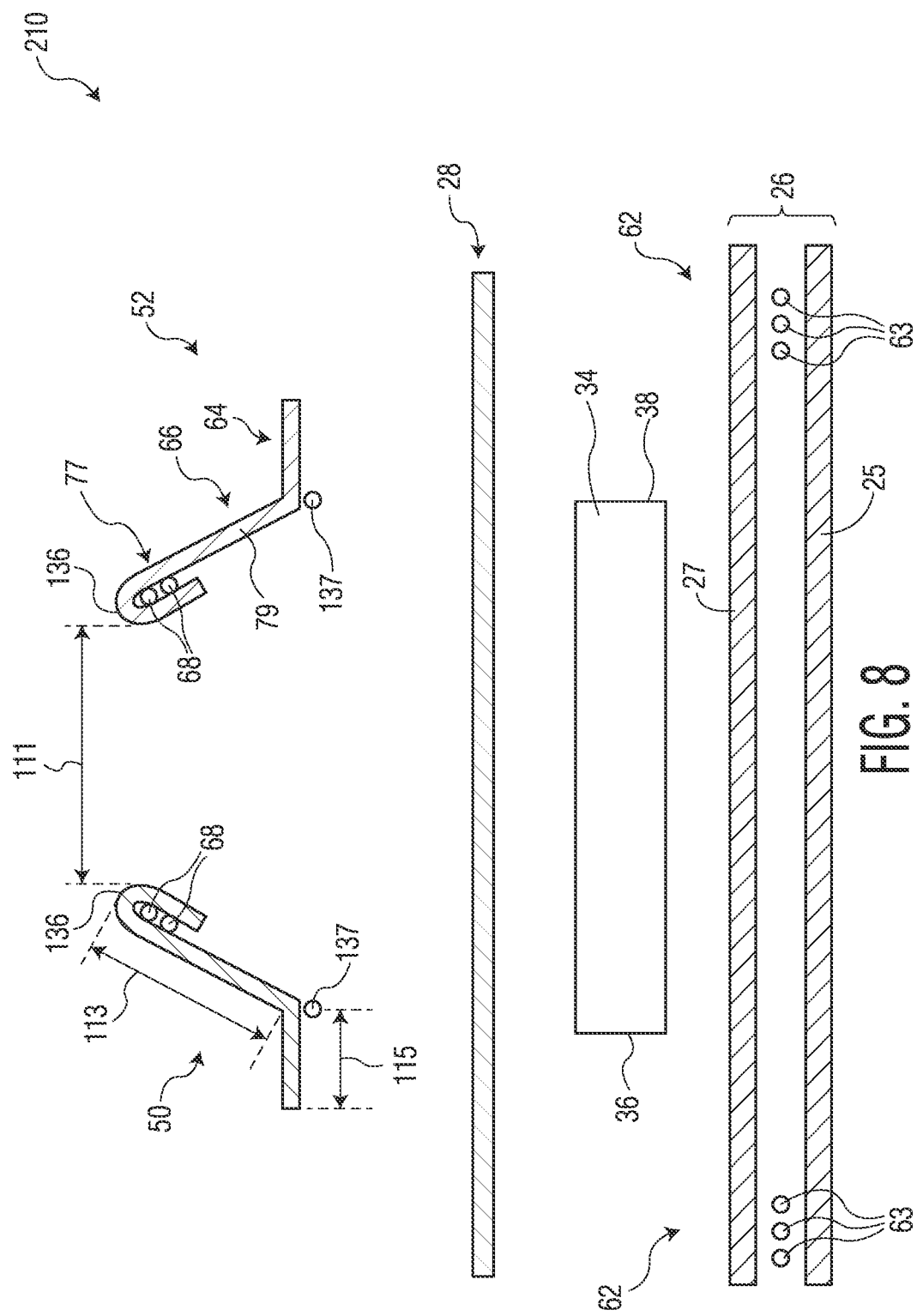
FIG. 8 is a cross-sectional view taken along line 8-8 of the article of FIG. 7.
Figure 9:
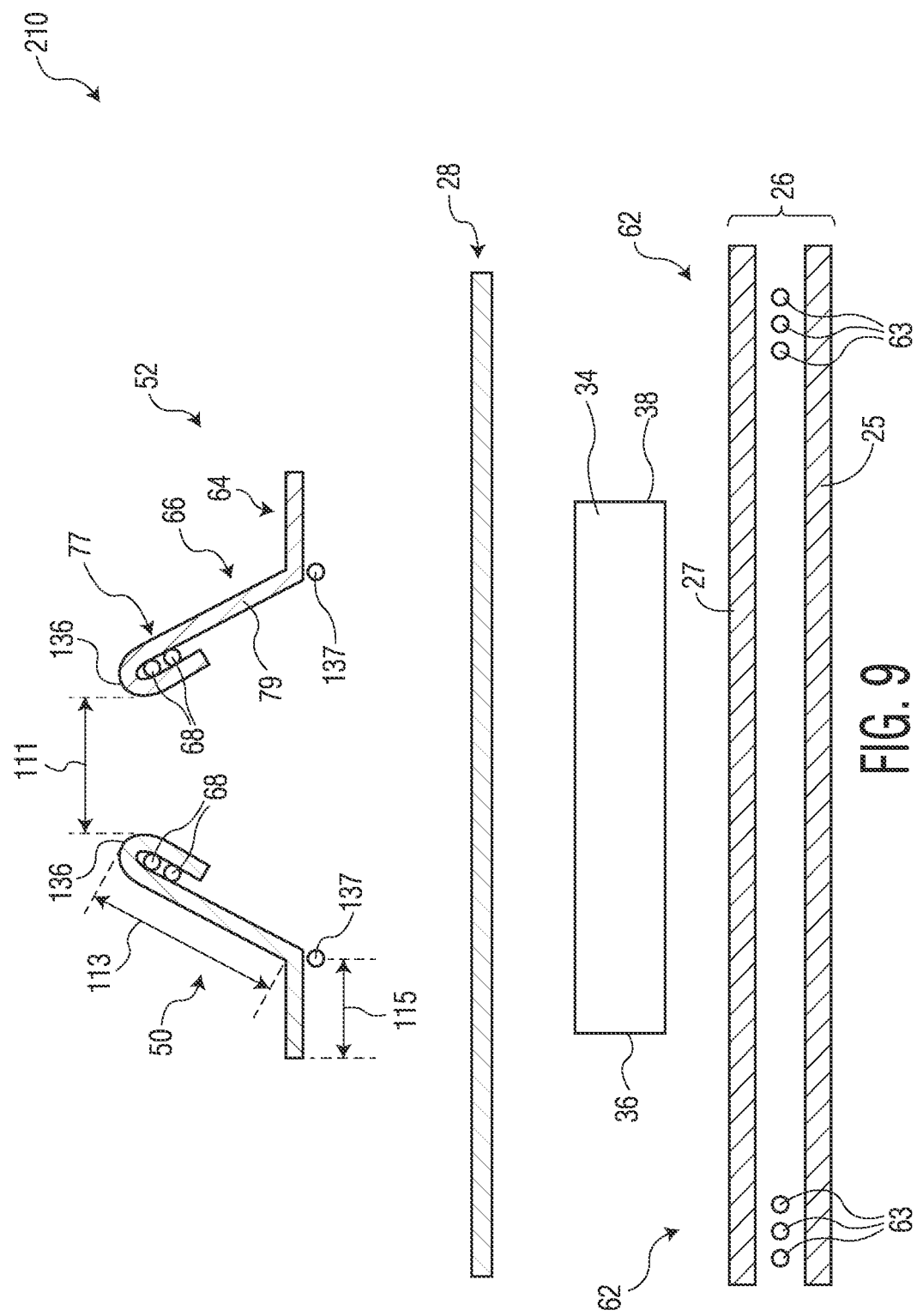
FIG. 9 is a cross-sectional view taken along line 9-9 of the article of FIG. 7.

FIGS. 7-9 depict another embodiment of an absorbent article 210 comprising curved containment flaps 50, 52. The FIG. 7 depicts the exemplary absorbent article 210 in a laid-flat, stretched configuration while the FIGS. 8 and 9 depict cross-sections of the article 210 of FIG. 7 as viewed along lines 8-8 and 9-9, respectively. The embodiment of article 210 in FIGS. 7-9 is similar to the article 110 in FIGS. 4-6, except that in the embodiment of FIGS. 7-9, the article 210 comprises curved barrier adhesives 137, which can be seen clearly in FIG. 7.

Where the curvature of the barrier adhesives 137 of article 210 matches the curvature of the laminates 77 forming the containment flaps 50, 52, the flap height 113 of the flaps 50, 52 will not vary along the length of the flaps 50, 52, as it did in the embodiment of article 110 of FIGS. 4-6. Although, the curvature of the laminates 77 will still result in a varying projection portion spacing 111. These features can be seen clearly in FIGS. 8 and 9, where the projection portion spacing 111 varies, while the flap heights 113, and correspondingly the proximal portion lengths 115, do not vary. Depending on the particular design of the article 110, the desired curvature of the laminates 77, along with straight barrier adhesives 137, may be result in portions of the containment flaps 50, 52 having flap heights 113 which are too large such that the flaps 50, 52 become ineffective at gasketing the wearer and containing bodily exudates. In such embodiments, the design of the article 210 of FIGS. 7-9 may be beneficial in maintain a useful flap height 113 while allowing for curvature of the laminates 77 to produce the varying projection portion spacing 111.

Of course, in at least some embodiments, the barrier adhesives 137 may be curved but the curvature may not exactly match the curvature of the laminates 77. For example, the barrier adhesives 137 may have a smaller amount of curvature than the laminates 77. In such embodiments, the flap height 113 may vary along the length of the flaps 50, 52, but the flap height 113 may be controlled such that the heights 113 along the entire lengths of the flaps 50, 52 do not get above the useful flap heights.

Also like in the embodiments of articles 210, in some embodiments of the article 310, the portions of the laminates 77 outboard of the barrier adhesive 137, as shown in FIG. 7, may be bonded to the chassis 11 so as to not allow any free edge portions of the laminates 77. Such bonding may be accomplished by having a wide barrier adhesive 137 which covers the portions of the laminates 77 which are disposed outboard of the proximal end portions 64a. In other embodiments, a separate adhesive region may extend along the base portion distal ends 64b. For example, an adhesive bead may be curved to match the curvature of the base portion distal ends 64b to secure at least the base portion distal ends 64b to the chassis 11.

Figure 10:
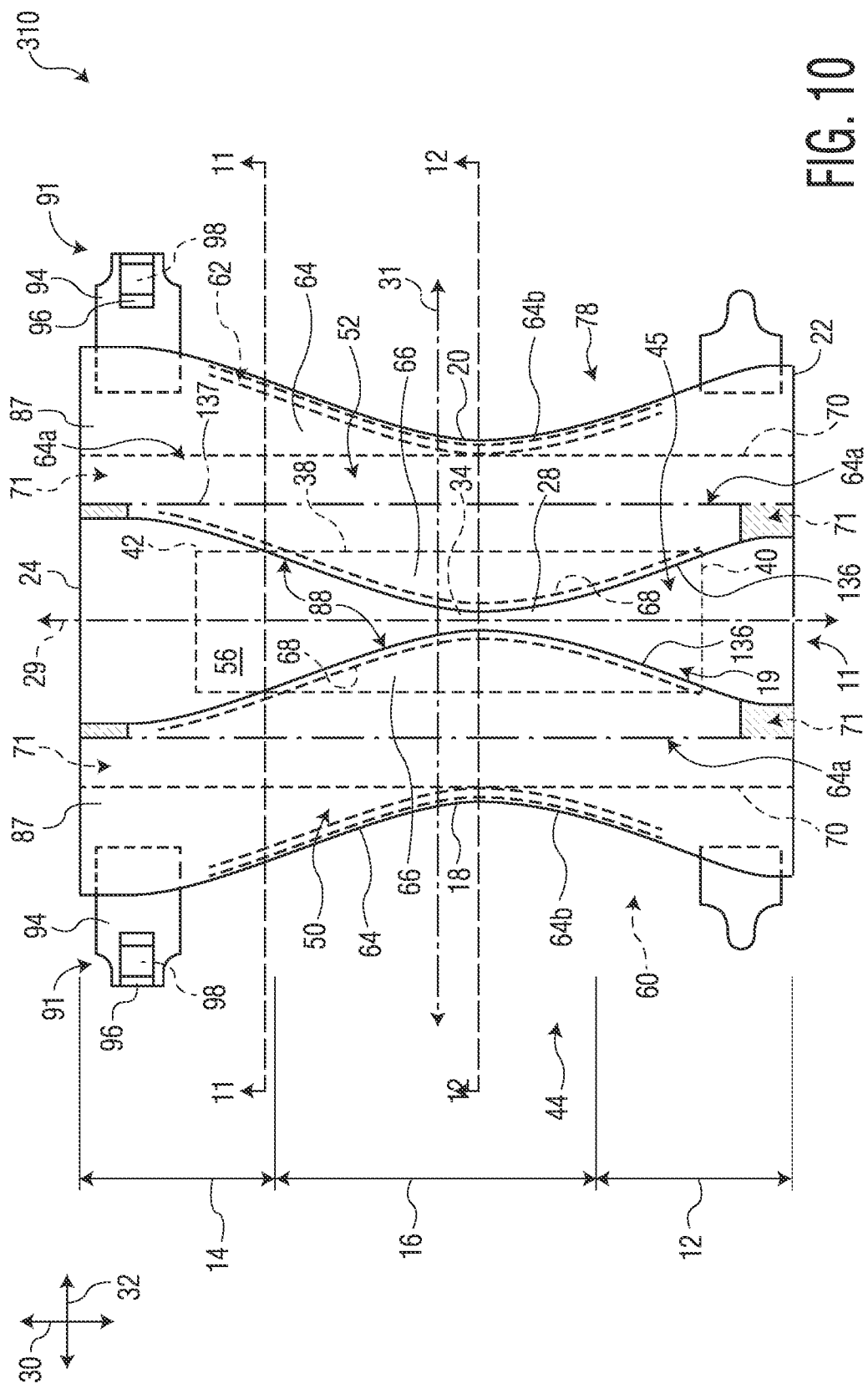
FIG. 10 is an exemplary top plan view of another embodiment of an absorbent article according to aspects of the present disclosure, in a stretched, laid flat, unfastened condition.
Figure 11:
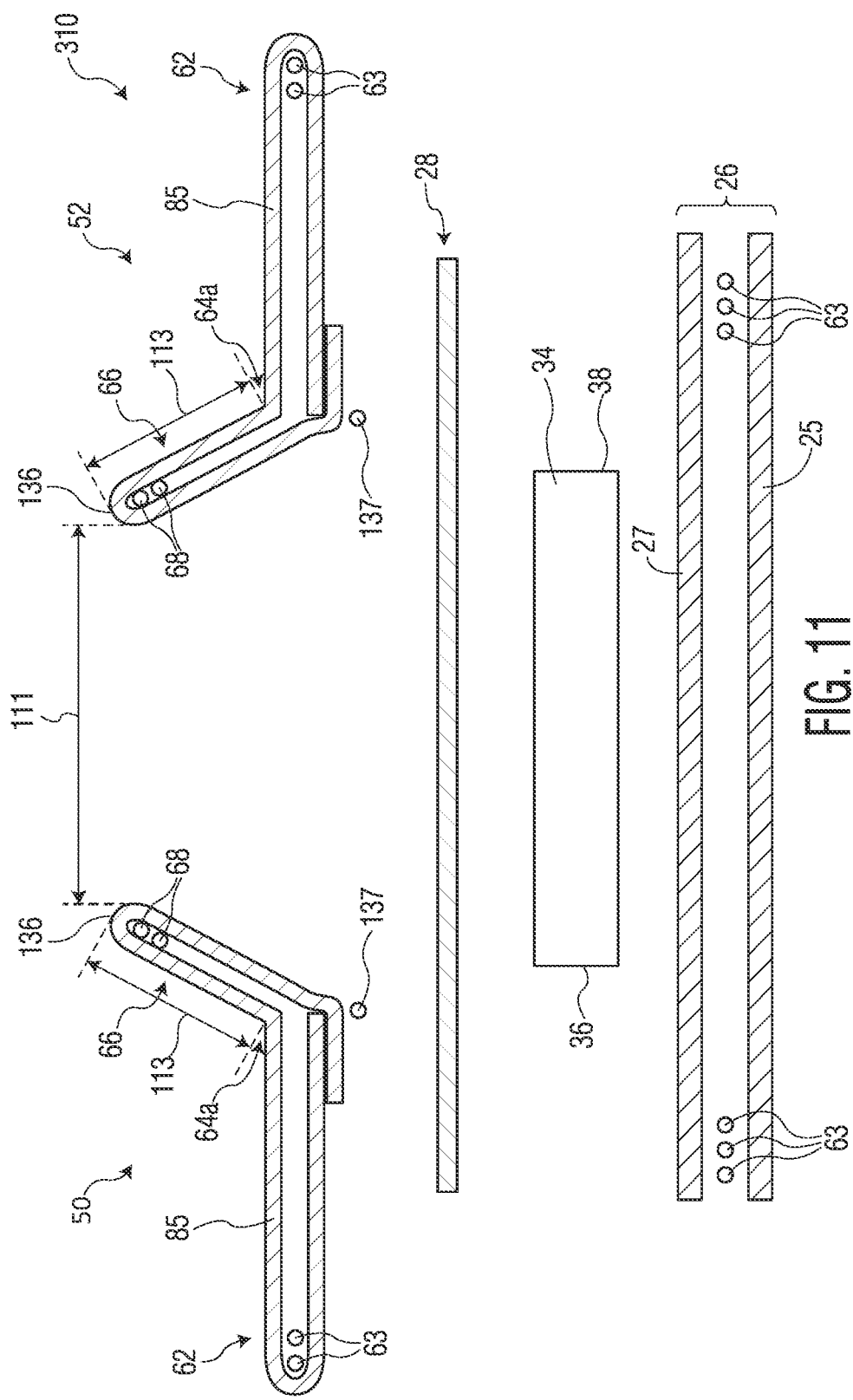
FIG. 11 is a cross-sectional view taken along line 11-11 of the article of FIG. 10.
Figure 12:
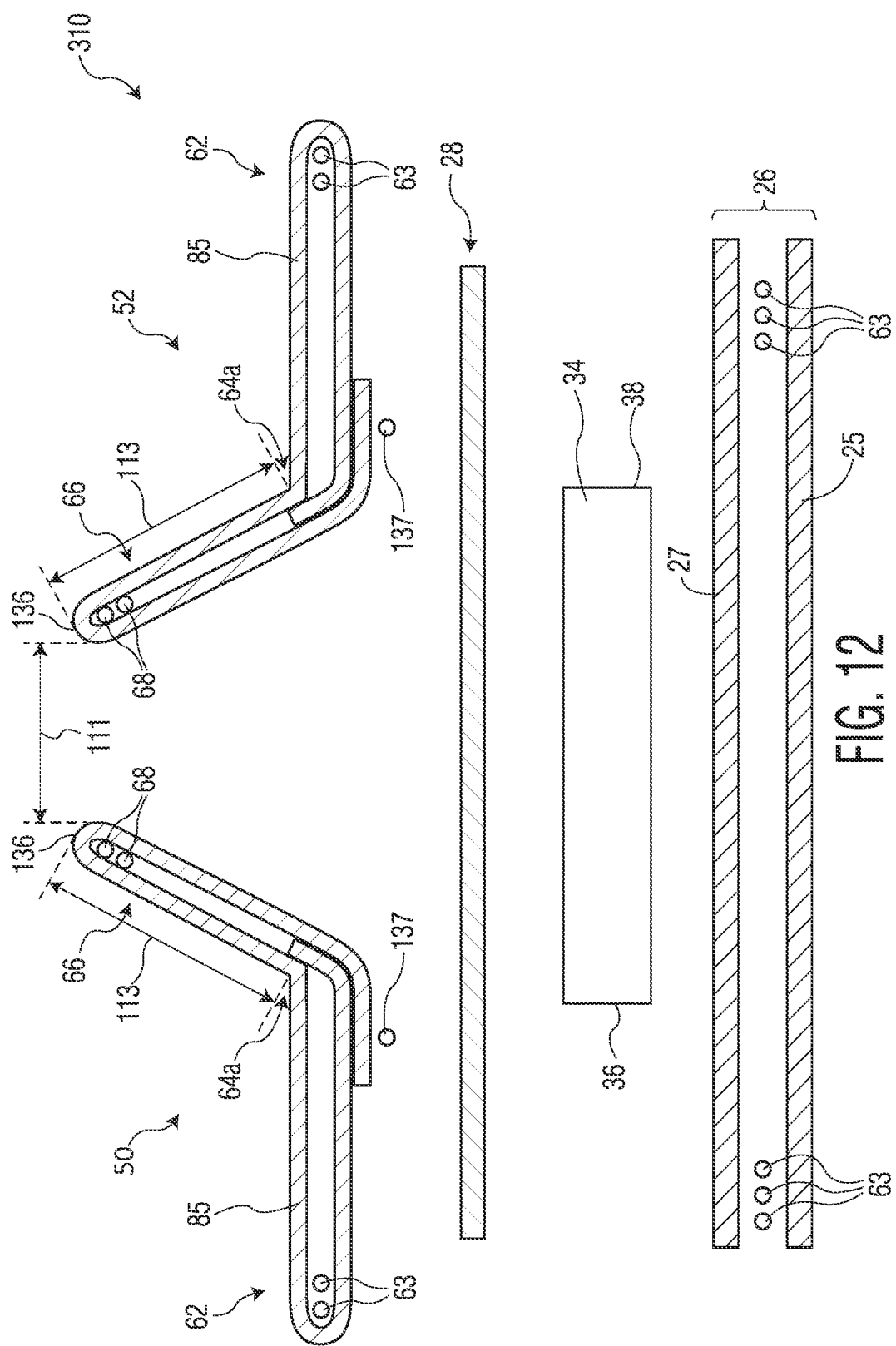
FIG. 12 is a cross-sectional view taken along line 12-12 of the article of FIG. 10.

FIGS. 10-12 depict still another exemplary absorbent article 310 according to aspects of the present disclosure. FIG. 10 depicts the exemplary absorbent article 310 in a laid-flat, stretched configuration while the FIGS. 11 and 12 depict cross-sections of the article 310 of FIG. 10 as viewed along lines 11-11 and 12-12, respectively. In the embodiment of article 310 of FIGS. 10-12, the article 310 comprises both curved leg cuffs 62 and curved containment flaps 50, 52.

As best seen in FIGS. 11 and 12, the article 310 comprises elasticized laminates 87, each of which form a combined leg cuff 62 and containment flap 50 or 52 laminate. The laminates 87 may be formed separately from the chassis 11 and then attached to the chassis 11 to form the leg cuffs 62 and the containment flap 50 or 52. The elasticized laminates 87 can comprise a combined containment flap and leg cuff material 85 with one or more elastomeric members 63 and one or more elastomeric members 68 disposed between the material 85. In some embodiments, the material 85 may be folded over to sandwich the members 63 and 68 between a top layer of the material 85 and a bottom layer of the material 85, as in FIGS. 11 and 12. In other embodiments, the material 85 may comprise two separate pieces, which are bonded together with the members 63 and 68 disposed therebetween to form the laminates 87. The elastomeric members 63 and 68 are secured within the laminates 87 through adhesive and/or mechanical bonds. Although not explicitly shown, the material 85 may be bonded together at locations other than proximate the elastomeric members 63, 68 as needed to maintain the integrity of the laminates 87. For example, where the material 85 comprises a single, folded piece of material, at least the ends of the material 85 may be bonded to the material 85 so there are no loose ends hanging off the laminates 87. In general, the elasticized laminates 87 may be formed such that the laminates 87 have a uniform width along their length—although this is not required in all embodiments.

The laminates 87 may be attached to the chassis 11 along barrier adhesives 137. Similarly to other embodiments of the present disclosure, just prior to attachment to the chassis 11, the elasticized laminates 87 may be oscillated back and forth to impart a curve to the laminates 87. This imparted curve is then maintained as the laminates 87 are bonded to the chassis 11 along barrier adhesives 137. This curvature of the laminates 87 results in both curvature of the article longitudinal side edges 18, 20 and of the containment flaps 50, 52. This curving of the containment flaps 50, 52 results in varying projection portion spacing 111 along the length of the article 310, as can be best seen in FIGS. 11 and 12.

As shown in the embodiment of FIG. 10, the barrier adhesives 137 may be applied in a straight line. In these embodiments, the containment flap heights 113 may vary along the length of the flaps 50, 52, as can be seen in FIGS. 11 and 12. The specific variation in the flap heights 113 may be similar to those described with respect to the embodiments of FIGS. 4-6. Although, in other embodiments, the barrier adhesives 137 may be applied in a curved fashion, for example in a similar manner as described with respect to FIGS. 7-9.

In still further embodiments, the laminates 87 may be further attached to the chassis along the chassis outer edges 70. For instance, an adhesive bead may be located along the chassis outer edges 70 to ensure close contact between the laminates 87 and the chassis along the chassis outer edges 70 so the chassis outer edges 70 are not free to move independent of the laminates 87. In further embodiments, an adhesive may cover the body-facing surface 19 of the chassis 11 between the barrier adhesives 137 and the chassis outer edges 70 to ensure close contact between the chassis 11 and the laminates 87.

One advantage of the embodiment of FIGS. 10-12 is that only a single elasticized laminate 87 need be formed and curved in order to provide the advantages to an absorbent article of having both curved outer longitudinal side edges 18, 20 and curved containment flaps 50, 52. However, one of the limitations of these embodiments is that because the laminates 87 form both the leg cuffs 62 and the flaps 50, 52, the curvature of the cuffs 62 and the flaps 50, 52 are the same.

Figure 13:
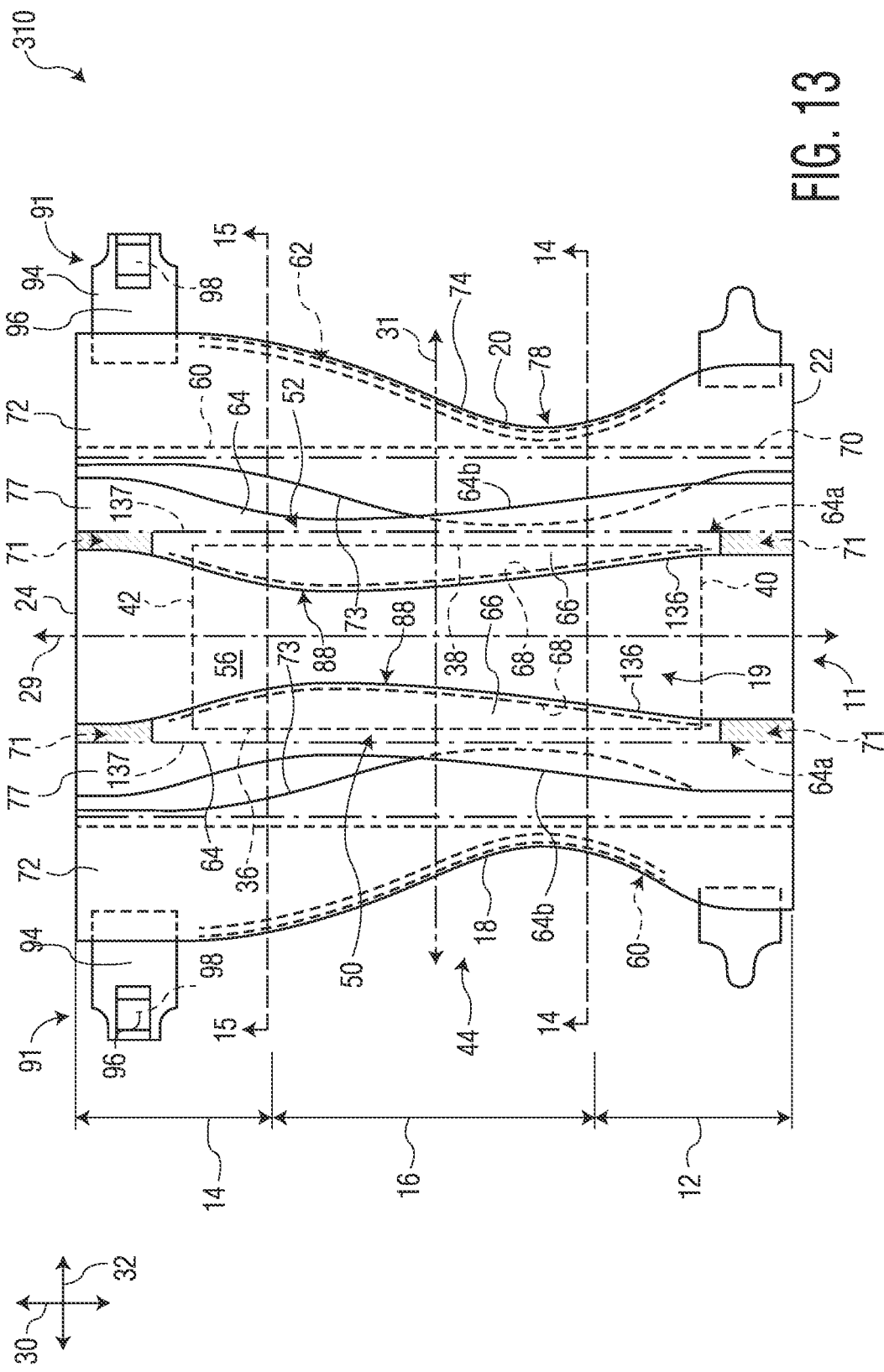
FIG. 13 is an exemplary top plan view of another embodiment of an absorbent article according to aspects of the present disclosure, in a stretched, laid flat, unfastened condition.
Figure 14:
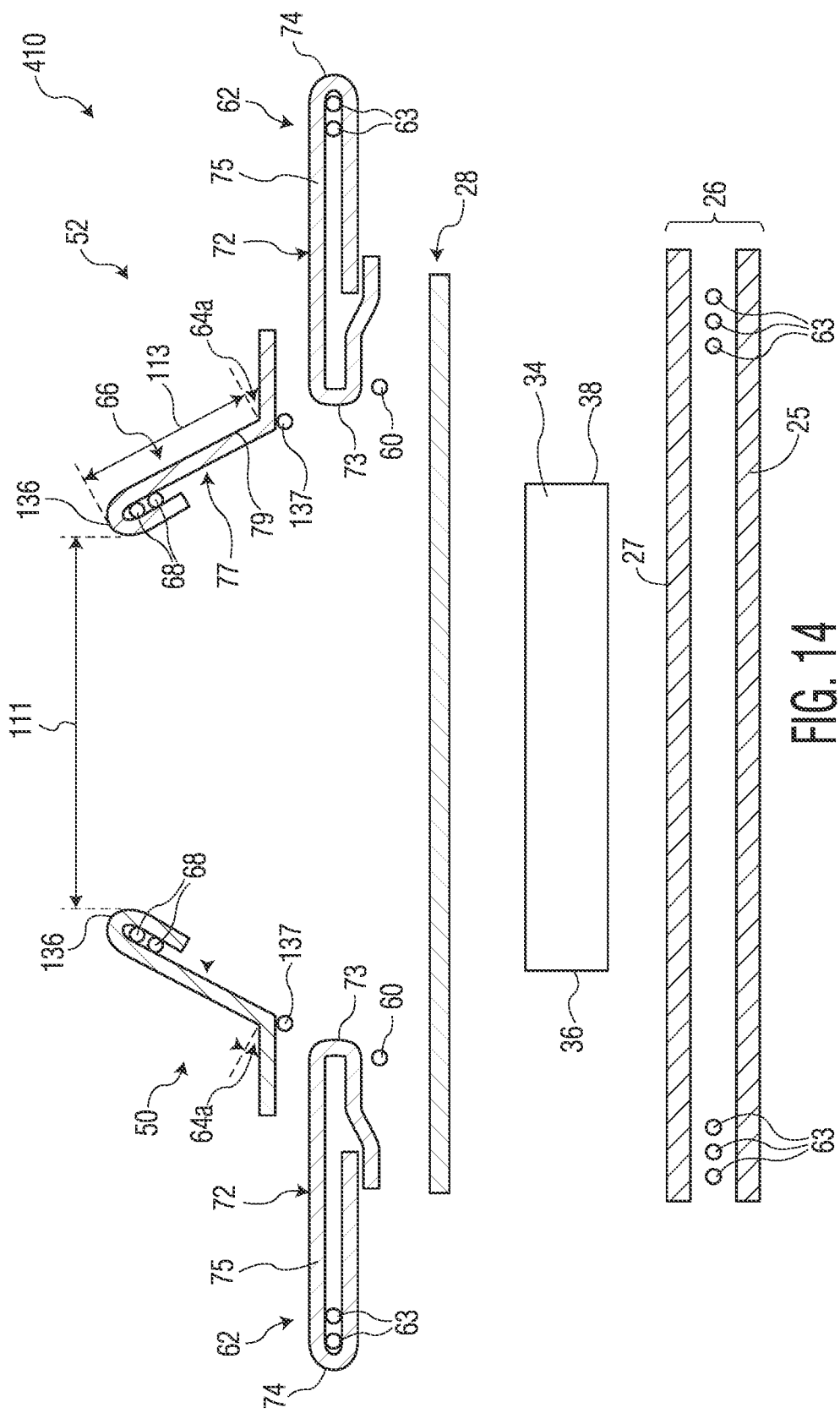
FIG. 14 is a cross-sectional view taken along line 14-14 of the article of FIG. 13.
Figure 15:
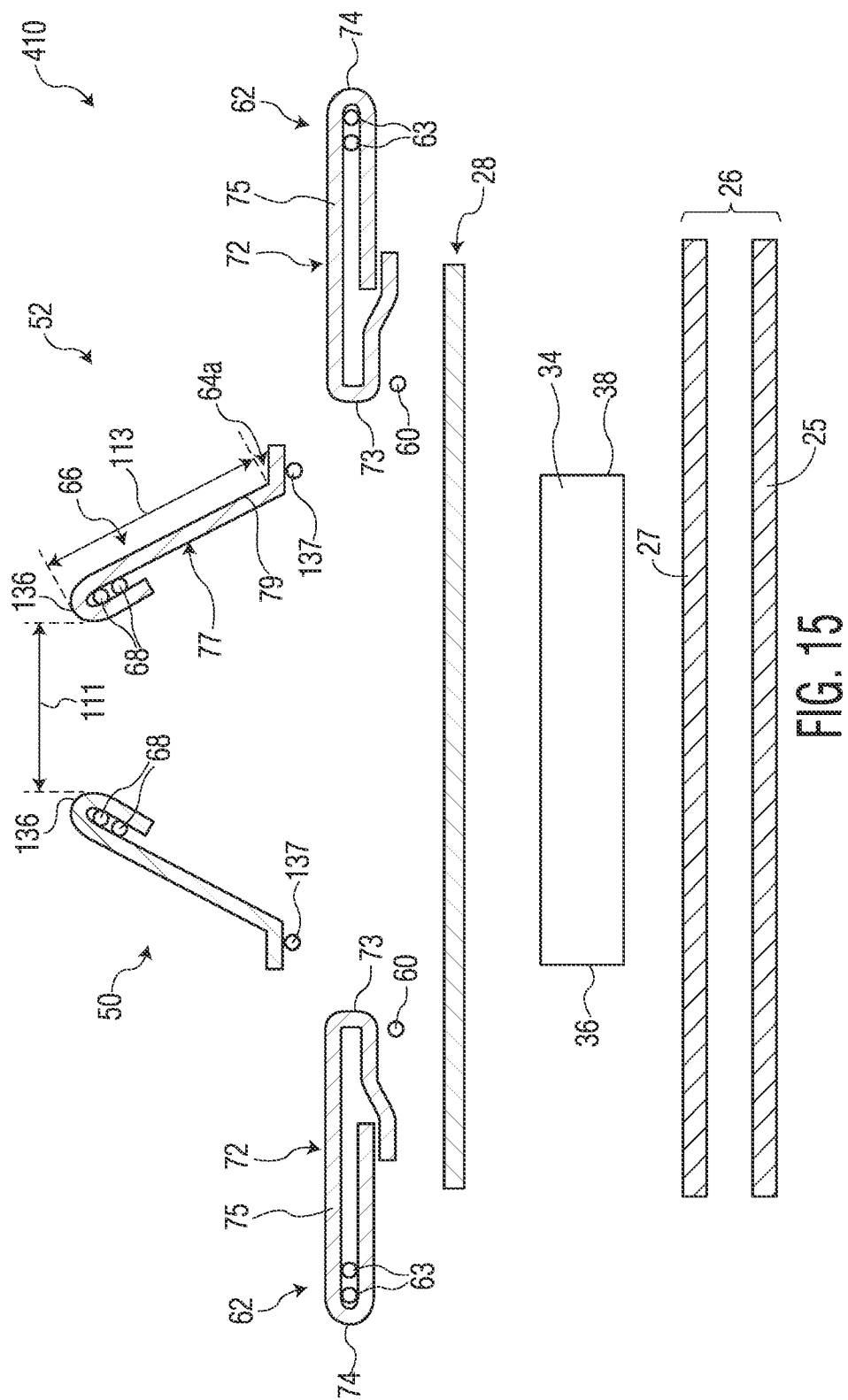
FIG. 15 is a cross-sectional view taken along line 15-15 of the article of FIG. 13.

FIGS. 13-15 depict another exemplary absorbent article 410 comprising separate elasticized laminates 72, 77 which form the leg cuffs 62 and the flaps 50, 52, respectively. FIG. 13 depicts an exemplary absorbent article 410 in a laid-flat, stretched configuration while the FIGS. 14 and 15 depict cross-section views of the article 410 of FIG. 13 as viewed along lines 14-14 and 15-15, respectively.

As can be seen, each of the laminates 72, 77 may be formed separately from the chassis 11 and attached separately to the chassis to form the leg cuffs 62 and the flaps 50, 52, respectively—such as described with respect to the embodiments of FIGS. 2-12. The laminate 72 may comprise a laminate material 75 with one or more elastomeric members 63 disposed between the material 75, as described with respect to the embodiments of FIGS. 2-3. The laminate 77 may comprise a laminate material 79 with one or more elastomeric members 68 disposed between the material 79, as described with respect to the embodiments of FIGS. 4-9. The specific structures of the laminates 72, 77 may be similar to any of those described with respect to the embodiments of FIGS. 2-9, such as comprising one or more folds or comprising multiple separate pieces of material and the like. The elastomeric members 63 and 68 are secured within the laminates 72, 77 through adhesive and/or mechanical bonds. In general, the elasticized laminates 72, 77 may be formed such that the laminates 72, 77 have a uniform width along their length—although this is not required in all embodiments. Although, the width of the laminates 72, 77 may be different.

The laminates 72, 77 may be attached to the chassis 11 along bonds 60 and barrier adhesives 137, respectively. Similarly to other embodiments of the present disclosure, just prior to attachment to the chassis 11, the elasticized laminates 72, 77 may be oscillated back and forth to impart a curve to the laminates 72, 77. This imparted curve is then maintained as the laminates 72, 77 are bonded to the chassis 11 along the bonds 60 and the barrier adhesives 137. Although shown as straight lines in FIG. 13, the bonds 60 and/or the barrier adhesives 137 could be curved in different embodiments, for example similar to those described with respect to FIGS. 2-3 and 7-9.

According to embodiments of the article 410 of FIGS. 13-15, the laminates 72, 77 may be oscillated independently of one another. This allows for imparting independent curvatures to the laminates 72, 77, as shown in FIG. 13. For example, the apex 78 of the cuffs 62 is shown disposed in the front half of the article 410, while the apex 88 of the flaps 50, 52 is shown disposed in the rear half of the article 410. Such a configuration may be beneficial from both a fit perspective, positioning the apex 78 of the cuffs 62 in a first location to provide a better fit to the article 410, and from a skin benefit perspective, positioning the apex 88 of the flaps 50, 52 in a second, different location so as to protect more of the wearer's skin from contacting fecal material.

In some embodiments, the differing curvature may result in a configuration where the laminates 72, 77 overlap along a portion of their length and do not overlap along a portion of their length, as can be seen in FIGS. 13-15. According to some embodiments, the laminates 72 may be disposed beneath the laminates 77, and the laminate inner edges 73 may be disposed wholly outboard of the proximal end portions 64a of the containment flaps 50, 52 such that the barrier adhesive 137 bonds the flaps 50, 52 directly to the body-facing surface 19 of the chassis 11, such as to the body-side liner 28. In some designs, the bonding between the containment flaps 50, 52 (e.g. laminates 77) and the body-facing surface 19 may represent a liquid-impermeable bond such that bodily exudates cannot wick or leak beyond (e.g. outboard) the proximal end portions 64a of the flaps 50, 52. In these designs, it is important for the laminate inner edges 73 to be disposed outboard of the proximal end portions 64a (and thus, outboard of the barrier adhesive 137) so as not to interfere with this liquid-impermeable barrier created by the barrier adhesive 137 bonding the proximal end portions 64a of the flaps 50, 52 to the body-facing surface 19 of the chassis 11. In other embodiments, however, at least a portion of the laminate inner edges 73 may extend inboard of the barrier adhesive 137. In such embodiments, the laminate material 75 may be a hydrophobic material which does not wick fluid (or may be made hydrophobic through application of one or more hydrophobic coatings). In alternative embodiments, adhesive may be strategically disposed between and throughout the laminate material 75 in sufficient quantity to form a liquid-impermeable barrier within the laminates 72, thereby forming a liquid-impermeable barrier between the laminates 72 and the body facing surface 19 of the chassis and between the laminates 72 and the containment flaps 50, 52.

In some alternative embodiments, the laminates 72 may be disposed on top of the laminates 77. In such embodiments, the laminates 77 may be bonded directly to the body-facing surface 19 of the chassis 11 by the barrier adhesive 137, forming a liquid impermeable barrier. In these embodiments, the laminate inner edges 73 may not extend inboard of the proximal end portions 64a of the flaps 50, 52 so as not to interfere with any lifting of the projection portions 66 during use so that the projection portions 66 may properly gasket the wearer's body to prevent leakage. In other embodiments, the laminate inner edges 73 may extend inboard of the proximal end portions 64a as long as the bond 60 is disposed outboard of the proximal end portions 64a and wherein the laminate inner edges 73 do not extend inward further than the projection portion distal ends 136, when the article 410 is in a laid-flat, stretched configuration.

Curving the Elasticized Laminates:

One of the challenges in forming the above described absorbent articles 10, 110, 210, 310, and 410, is imparting the curvature to the described elasticized laminates 72, 77, and 87 and attaching the laminates 72, 77, and 87 to the chassis 11 in a continuous manufacturing process. Many options exist for oscillating elastomeric ribbons or elastomeric strands. However, the structures described with respect to FIGS. 1-15 require oscillating elasticized laminate structures including both elastomeric members and laminate materials. It had been found that such current elastomeric ribbon or strand oscillating devices or methods are not able to impart the desired curvature to the elasticized laminates of the present disclosure without resulting in folds or wrinkles in the laminates.

Figure 16:
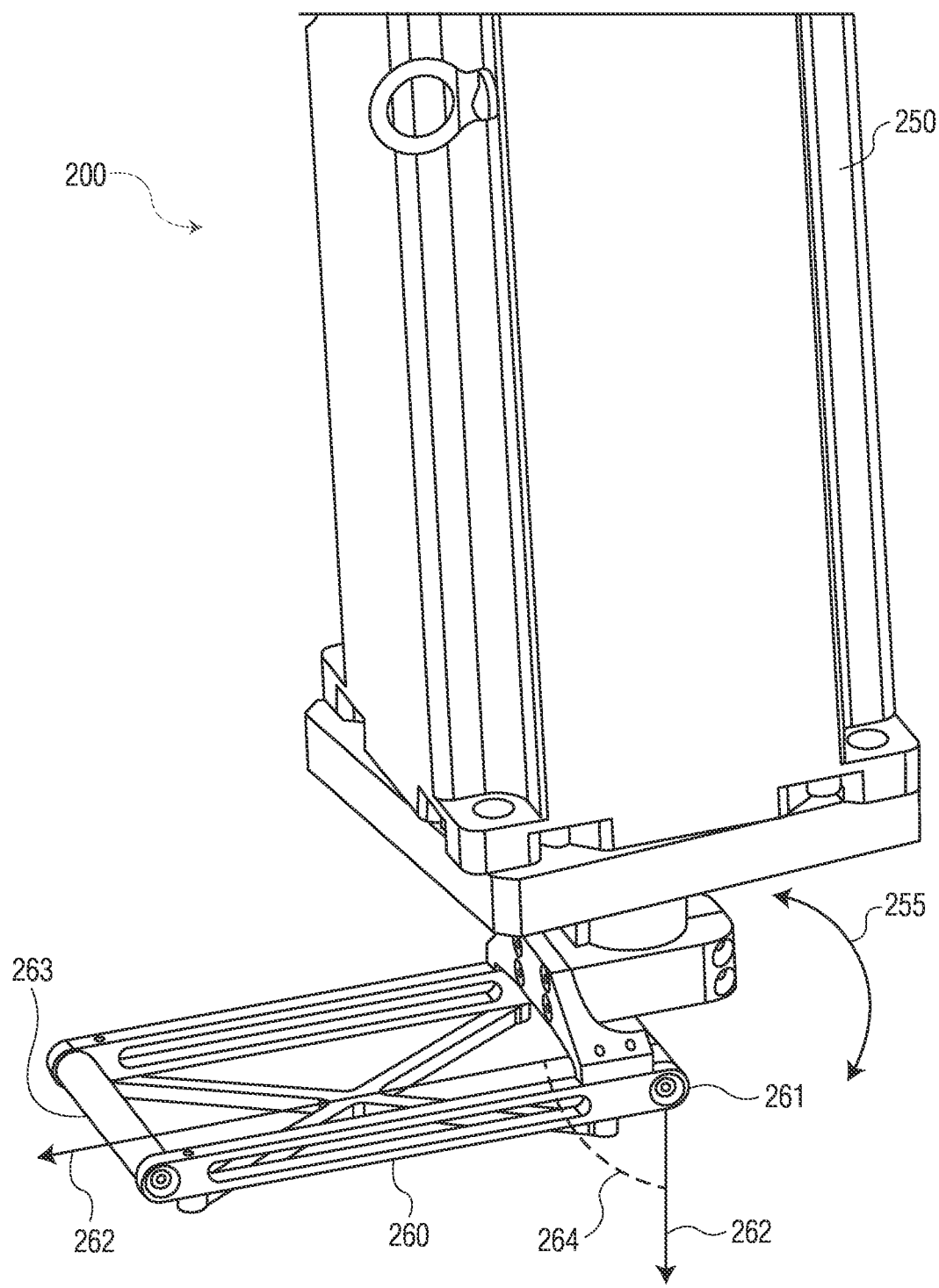
FIG. 16 is a side perspective view of an exemplary laminate oscillating apparatus, according to aspects of the present disclosure.

FIG. 16 depicts exemplary laminate oscillating apparatus 200, which may be used to impart a curvature to the elasticized laminates of the present disclosure without causing folding or wrinkling of the laminates such that the articles 10, 110, 210, 310, and 410 of the present disclosure may be formed during a continuous manufacturing process. FIG. 16 depicts oscillator motor 250 and laminate guide 260. The oscillator motor 250 may operate to swing the laminate guide 260 in a side-to-side motion, as indicated by arrows 255 while an elasticized laminate, such as laminates 72, 77, and 87 of the present disclosure, traverses through the laminate guide 260. This side-to-side motion imparts a curvature to the elasticized laminate as it traverses through the laminate guide 260.

To help the laminate oscillating apparatus 200 be effective at imparting the curvature to the elasticized laminates 72, 77, and 87 without forming folds or wrinkles, the elasticized laminates 72, 77, and 87 may traverse through the laminate guide 260 along the web path 262 shown in FIG. 16. The laminate guide 260 may comprise a proximal end 261 where the laminates 72, 77, and 87 come into contact with the laminate guide 260 and a distal end 263 where the laminates 72, 77, and 87 exit the laminate guide 260.

It has been found that it is important for the web path 262 to form an angle 264 between where the web path 262 enters the web guide 260 (e.g. where the web path 262 contacts the proximal end 261) and the web path 262 as it travels through the web guide 260. A useful range for angle 264 may be between about 120 degrees to greater than about 0 degrees. In other embodiments, the angle 264 may be between about 105 degrees to greater than about 0 degrees, or between about 90 degrees to greater than about 0 degrees. These ranges of angles allow for sufficient wrapping of the laminates 72, 77, and 87 around the proximal ends 261 of the web guide 260 to ensure adequate tension is maintained on the laminates 72, 77, and 87 as they traverse through the laminate guide 260. Adequate tension is needed so that the oscillating motion of the laminate guide 260 does not cause folds or wrinkles to form in the traversing elasticized laminates 72, 77, and 87.

In some embodiments, it has been found that an exit idler roll placed between the distal end 263 and a point where the laminates 72, 77, and 87 are attached to an absorbent article chassis or absorbent assembly in a manufacturing process may be beneficial to help maintain the imparted curvature of the laminates 72, 77, and 87. In such embodiments, it has been found that the laminates should wrap the exit idler roll for between about one-quarter and about one-half of the circumference of the idler roll in order for the laminates 72, 77, and 87 to both sufficiently maintain their curvature and to prevent folding of the edges of the laminates 72, 77, and 87.

Figure 17:
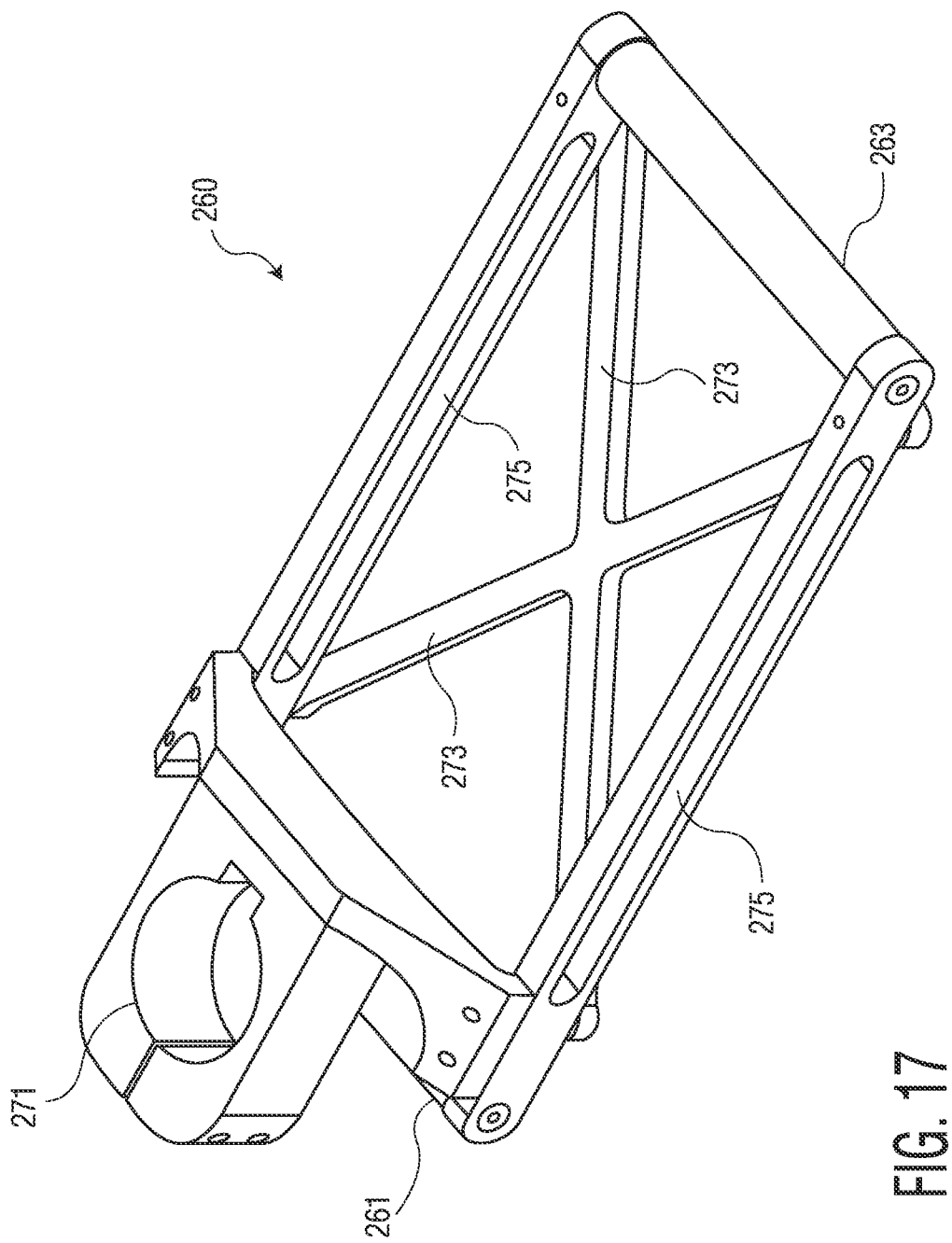
FIG. 17 is a perspective view of an exemplary web guide of the laminate oscillating apparatus of FIG. 16.

FIG. 17 depicts laminate guide 260. In general, laminate guide 260 may extend between proximal end 261 and distal end 263. In at least some embodiments, the proximal and distal ends 261, 263 of the web guide 260 can be rollers to reduce friction between the laminate webs 72, 77, and 87 and the web guide 260. Support bars 275 may extend between the proximal and distal ends 261, 263. In at least some embodiments, the support bars 275 may include one or more cut-outs to reduce the weight of the support bars. The laminate guide 260 may further include support brace 273 in some embodiments, which may brace the support bars 275 and/or the proximal and distal ends 261, 263 to provide a desired level of stiffness to the laminate guide 260. For example, it is desired that the laminate guide 260 not bend or flex while moving at high speeds. The laminate guide 260 may further include connector 271, which may allow the laminate guide 260 to be coupled to a motor, such as a rotary servomotor.

In general, the laminate guide 260 is designed to have a very low rotational inertia. As described, the support bars 275 may include one or more cut-outs to remove material. Additionally, a width of the proximal and distal ends 261, 263 of the laminate guide 260 between the support bars 275 may be less than 5% greater than a width of the laminate materials used with the laminate guide 260. Further, the laminate guide 260 may comprise one or more light, strong materials, such as aluminum, carbon fiber, or other similar classes of materials which are low-weight, high-strength materials. These properties combined give the laminate guide 260 a relatively low rotational inertia, thereby allowing the laminate guide 260 to be used at the very high speeds necessary for use in modern high-speed manufacturing processes.

Figure 18:
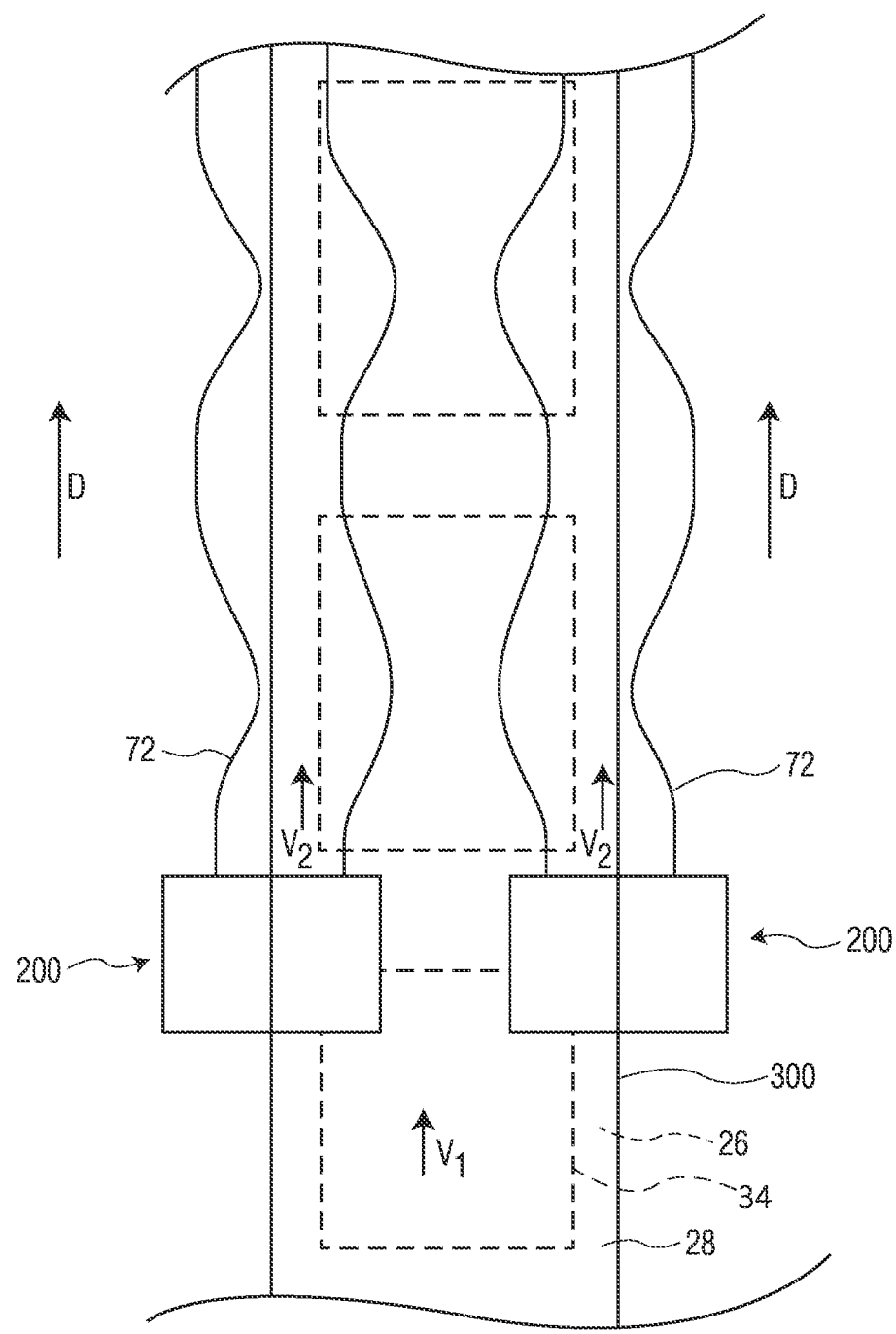
FIG. 18 is a plan view of a process of oscillating and attaching curved elastomeric laminate materials to a continuous stream of absorbent assemblies, according to aspects of the present disclosure.

FIG. 18 depicts an exemplary process of attaching continuous elasticized laminates to continuous length of absorbent assemblies. For example, FIG. 18 depicts absorbent assemblies 300 moving in the machine direction, indicated by arrows D. The assemblies 300 comprise bodyside liner 28, outer cover 26, and an absorbent body 34 sandwiched between the bodyside liner 28 and the outer cover 26.

FIG. 18 further depicts oscillating apparatuses 200 disposed adjacent side edges of the continuous length of assemblies 300. The oscillating apparatuses 200 work to oscillate elasticized laminates 72 back and forth in a cross-machine direction generally perpendicular to the machine direction D, imparting a curvature to the laminates 72. The oscillating apparatuses 200 are configured to operate in opposed fashions so that the laminates 72 are imparted with opposing curvatures. In order to compensate for the extra material needed for the laminates 72 to span the same machine direction distance, the laminates 72 may move at a speed V2 which is greater than the speed V1. The speed V1 is the speed at which the continuous length of assemblies 300 moves in the machine direction. For example, an arc-length of the laminates 72 in a finished absorbent article product may be measured and compare to the overall article length. The arc-length of the laminates are the total length of an edge of one of the laminates. The speed V2 should be set to be faster than the speed V1 by a percentage amount equal to the difference between the arc-length of the laminates 72 and the overall article length, divided by the article length. In some embodiments the speed V2 may vary throughout the oscillation pattern of the oscillating apparatuses 200 based on a current speed of the oscillation pattern. For example, as the oscillating apparatuses 200 are rotating at a relatively high speed, the speed V2 may be relatively greater than the speed V2 at times which the oscillating apparatuses 200 are rotating at a relatively lower speed.

After exiting the oscillating apparatuses 200, e.g. after exiting the distal ends 263 of the web guides 260 of the oscillating apparatuses 200, the laminates 72 are subsequently attached to the continuous length of assemblies 300. In a preferred embodiment, the laminates 72 travel no more than about 15 cm before being attached to continuous length of assemblies 300 after exiting from the distal end 263 of the web guide 206. Although, this specific limitation is not necessary in all embodiments. Generally, the shorter the distance the laminates 72 travel between distal end 263 of the web guide 260 and the point where the laminates 72 are attached to the continuous length of assemblies 300, the more effectively the imparted curvature of the laminates 72 is maintained. The continuous length of assemblies 300, along with the attached continuous lengths of oscillated laminates 72, may then be separated in individual articles according to any commonly known techniques in the art.

Although FIG. 18 only depicts one exemplary method of connecting elasticized laminates 72 to a continuous length of absorbent assemblies 300, it should be understood that similar processes may be employed to produce any of the articles 10, 110, 210, 310, and 410 of the present disclosure. For example, the oscillating apparatuses 200 may be configured to oscillate elasticized laminates such as those described with respect to any of FIGS. 1-15, which may be attached to the continuous length of absorbent assemblies 300 to form any of the articles 10, 110, 210, 310, and 410. In some embodiments, multiple oscillating apparatuses 200 may be employed to oscillate multiple elasticized laminates to produce absorbent articles such as described with respect to FIGS. 13-15.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

EMBODIMENTS

In a first embodiment, a method of forming an absorbent article may comprise moving a stream of connected absorbent assemblies in a machine direction, the absorbent assemblies comprising: a bodyside liner, an outer cover, and an absorbent body disposed between the bodyside liner and the outer cover, the absorbent body having a length in the machine direction that is greater than a width in a cross-machine direction. The first embodiment may further comprise moving a first pair of elasticized laminates in the machine direction, each of the first pair of elasticized laminates comprising: a laminate material comprising a fold to form a laminate material top layer and a laminate material bottom layer, and an elastomeric member disposed between the laminate material top layer and the laminate material bottom layer. The first embodiment may still further comprise oscillating, with a laminate oscillating device, each of the first pair of elasticized laminates in the cross-machine direction to impart a curvature to each of the first pair of elasticized laminates, bonding each of the first pair of elasticized laminates to the stream of connected absorbent assemblies while maintaining the imparted curvature such that at least a portion of the fold of each of the first pair of elasticized laminates is disposed outboard of longitudinal side edges of the stream of connected absorbent assemblies, and separating the stream of connected absorbent assemblies into individual absorbent articles, each article comprising a front region, a rear region, and a crotch region disposed between the front region and the rear region, wherein the fold and the elastomeric member of each elasticized laminate of each individual absorbent article extend in a curving manner throughout at least the crotch region of each individual absorbent article.

In a second embodiment, the elastomeric member of the first embodiment may comprise one or more elastomeric strands.

In a third embodiment, each of the first pair of elasticized laminates of the first or second embodiments may be bonded to the stream of connected absorbent assemblies along a straight bond line.

In a fourth embodiment, each of the first pair of elasticized laminates of the first or second embodiments may be bonded to the stream of connected absorbent assemblies along a curving bond line.

In a fifth embodiment, the fold and the elastomeric member of each elasticized laminate of each individual absorbent article of any of the first through fourth embodiments may be disposed completely outboard of longitudinal side edges of a chassis of the individual absorbent articles.

In a sixth embodiment, each of the first pair of elasticized laminates of any of the first through fifth embodiments may further comprise a first group of one or more elastomeric members, and a second group of one or more elastomeric members spaced from the first group of elastomeric members, wherein each of the first pair of elasticized laminates may be attached to the stream of connected absorbent assemblies at a location between the first group of one or more elastomeric members, which form elasticized leg cuffs in the individual absorbent articles, and the second group of one or more elastomeric members, which form elasticized containment flaps in the individual absorbent articles.

In a seventh embodiment, any of the first through sixth embodiments may further comprise moving a pair of continuously extending elasticized containment flaps in the machine direction and bonding the pair of continuously extending elasticized containment flaps to the stream of connected absorbent assemblies, wherein the pair of elasticized containment flaps may cover at least a portion of each of the first pair of elasticized laminates.

In an eight embodiment, the bonded pair of continuously extending elasticized containment flaps of the seventh embodiment may each comprise a projection portion uncoupled to the stream of connected absorbent assemblies and a base portion coupled to the stream of connected absorbent assemblies, wherein the base portion may have a proximal end portion which defines a transition between the projection portion and the base portion, and wherein the continuously extending elasticized containment flaps may be bonded to the stream of connected absorbent assemblies such that first pair of elasticized laminates do not extend laterally inboard of the proximal end portions of the elasticized containment flaps.

In a ninth embodiment, each of the first pair of elasticized laminates of any of the first through eighth embodiments may have a constant cross-machine direction width.

In a tenth embodiment, each of the first pair of elasticized laminates of any of the first through ninth embodiments may traverse through the laminate oscillating device along a laminate web path, the laminate web path forming an angle of between about 120 degrees to greater than about 0 degrees.

In an eleventh embodiment, each of the first pair of elasticized laminates of any of the first through ninth embodiments may traverse through the laminate oscillating device along a laminate web path, the laminate web path forming an angle of between about 90 degrees to greater than about 0 degrees.

In a twelfth embodiment, a method of forming an absorbent article ma comprise moving a stream of connected absorbent assemblies in a machine direction, the absorbent assemblies comprising: a bodyside liner, an outer cover, and an absorbent body disposed between the bodyside liner and the outer cover, the absorbent body having a length in the machine direction that is greater than a width in a cross-machine direction. The twelfth embodiment may further comprise moving a first pair of elasticized laminates in the machine direction, each of the first pair of elasticized laminates comprising: a laminate material having first side edge and a second side edge, at least one of the first side edge and the second side edge being a folded edge, wherein the laminate material comprises a laminate material top layer and a laminate material bottom layer, and an elastomeric member disposed between the laminate material top layer and the laminate material bottom layer. The twelfth embodiment may still further comprise oscillating, with a laminate oscillating device, each of the first pair of elasticized laminates in the cross-machine direction to impart a curvature to each of the first and second side edges of each of the first pair of elasticized laminates, bonding each of the first pair of elasticized laminates to the stream of connected absorbent assemblies while maintaining the imparted curvature, and separating the stream of connected absorbent assemblies into individual absorbent articles, each article comprising a front region, a rear region, and a crotch region disposed between the front region and the rear region, wherein the first and second side edges and the elastomeric member of each elasticized laminate of each individual absorbent article extend in a curving manner throughout at least the crotch region of each individual absorbent article.

In a thirteenth embodiment, each of the first pair of elasticized laminates of the twelfth embodiment may form elasticized containment flaps in the individual absorbent articles.

In a fourteenth embodiment, each of the first pair of elasticized laminates of the thirteenth embodiment may be bonded to the stream of connected absorbent assemblies along a straight bond line.

In a fifteenth embodiment, each of the first pair of elasticized laminates of the thirteenth embodiment may be bonded to the stream of connected absorbent assemblies along a curving bond line.

In a sixteenth embodiment, any of the twelfth through fifteenth embodiments may further comprise moving a second pair of elasticized laminates in the machine direction, each of the second pair of elasticized laminates comprising: a laminate material having first side edge and a second side edge, at least one of the first side edge and the second side edge being a folded edge, wherein the laminate material comprises a laminate material top layer and a laminate material bottom layer and an elastomeric member disposed between the laminate material top layer and the laminate material bottom layer. The sixteenth embodiment may further comprise oscillating, with a laminate oscillating device, each of the second pair of elasticized laminates in the cross-machine direction to impart a curvature to each of the first and second side edges of each of the second pair of elasticized laminates and bonding each of the second pair of elasticized laminates to the stream of connected absorbent assemblies while maintaining the imparted curvature, wherein the curvature of each of the first pair of elasticized laminates may be different than the curvature of each of the second pair of elasticized laminates.

In a seventeenth embodiment, each of the second pair of elasticized laminates of the sixteenth embodiment may be bonded to the stream of connected absorbent assemblies such that at least a portion of the fold of each of the second pair of elasticized laminates is disposed outboard of longitudinal side edges of the stream of connected absorbent assemblies.

In an eighteenth embodiment, each of the first pair of elasticized laminates of any of the twelfth through seventeenth embodiments may be bonded to the stream of connected absorbent assemblies such that each of the first pair of elasticized laminates covers at least a portion of one of the second pair of elasticized laminates.

In a nineteenth embodiment, each of the first pair of elasticized laminates of any of the twelfth through eighteenth embodiments may further comprise a first group of one or more elastomeric members and a second group of one or more elastomeric members spaced from the first group of elastomeric members, wherein each of the first pair of elasticized laminates may be attached to the stream of connected absorbent assemblies at a location between the first group of one or more elastomeric members, which form elasticized leg cuffs in the individual absorbent articles, and the second group of one or more elastomeric members, which form elasticized containment flaps in the individual absorbent articles.

In a twentieth embodiment, each of the first pair of elasticized laminates of the nineteenth embodiment may be bonded to the stream of connected absorbent assemblies such that the first side edges of each of the first pair of elasticized laminates are disposed outboard of longitudinal side edges of the stream of connected absorbent assemblies.

We claim:

1. A method of forming an absorbent article comprising:
   moving a stream of connected absorbent assemblies in a machine direction having a central longitudinal axis between longitudinal side edges of the connected absorbent assemblies which extend in the machine direction, the absorbent assemblies comprising:
   a bodyside liner,
   an outer cover, and
   an absorbent body disposed between the bodyside liner and the outer cover, the absorbent body having a length in the machine direction that is greater than a width in a cross-machine direction;
   moving a first elasticized laminate in the machine direction, the first elasticized laminate comprising:
   a first laminate material comprising a laminate material top layer and a laminate material bottom layer, and
   an elastomeric member disposed between the laminate material top layer and the laminate material bottom layer;
   moving a second elasticized laminate in the machine direction, the second elasticized laminate comprising:
   a second laminate material comprising a laminate material top layer and a laminate material bottom layer, and
   an elastomeric member disposed between the laminate material top layer and the laminate material bottom layer;
   oscillating, with a laminate oscillating device, the first of elasticized laminate in the cross-machine direction to impart a curvature to the first elasticized laminate, the oscillation occurring within a single plane;
   oscillating, with the laminate oscillating device, the second elasticized laminate in the cross-machine direction to impart a curvature to each of the first and second side edges of the second elasticized laminate, the oscillation occurring within the single plane; and
   bonding each of the first elasticized laminate and the second elasticized laminate to the stream of connected absorbent assemblies to a same portion of the stream of connected absorbent assemblies located on a same side of the central longitudinal axis while maintaining the imparted first curvature of the first elasticized laminate and the imparted second curvature of the second elasticized laminate.

2. The method of claim 1, wherein the elastomeric member comprises one or more elastomeric strands.

3. The method of claim 1, wherein the first elasticized laminate is bonded to the stream of connected absorbent assemblies along a straight bond line.

4. The method of claim 1, wherein the first elasticized laminate is bonded to the stream of connected absorbent assemblies along a curving bond line.

5. The method of claim 1, wherein the elastomeric member of at least one of the first elasticized laminate and second elasticized laminate is disposed completely outboard of one of the longitudinal side edges of a chassis of the stream of connected absorbent assemblies.

6. The method of claim 1, wherein one of the first elasticized laminate and the second elasticized laminate forms a containment flap laminate of the stream of connected absorbent assemblies and wherein the other of the first elasticized laminate and the second elasticized laminate forms a leg cuff laminate of the stream of connected absorbent assemblies with the containment flap laminate covering.

7. The method of claim 1, wherein the first elasticized laminate has a constant cross-machine direction width.

8. The method of claim 1, wherein the first elasticized laminate traverses along a laminate web path extending through the laminate oscillating device, the laminate web path forming an angle of between about 120 degrees to greater than about 0 degrees between a portion of the laminate web path extending through the laminate oscillating device and a portion of the laminate web path just prior to where the first elasticized laminate contacts the laminate oscillating device.

9. The method of claim 1, wherein the first elasticized laminate traverses along a laminate web path extending through the laminate oscillating device, the laminate web path forming an angle of between about 90 degrees to greater than about 0 degrees between a portion of the laminate web path extending through the laminate oscillating device and a portion of the laminate web path just prior to where the first elasticized laminate contacts the laminate oscillating device.

10. The method of claim 1, wherein the first imparted curvature is different than the second imparted curvature.

11. A method of forming an absorbent article comprising:
moving a stream of connected absorbent assemblies in a machine direction having a central longitudinal axis between longitudinal side edges of the connected absorbent assemblies which extend in the machine direction, the absorbent assemblies comprising:
a bodyside liner,
an outer cover, and
an absorbent body disposed between the bodyside liner and the outer cover, the absorbent body having a length in the machine direction that is greater than a width in a cross-machine direction;
moving a first pair of elasticized laminates in the machine direction, each of the first pair of elasticized laminates comprising:
a laminate material having first side edge and a second side edge, at least one of the first side edge and the second side edge being a folded edge, wherein the laminate material comprises a laminate material top layer and a laminate material bottom layer; and
an elastomeric member disposed between the laminate material top layer and the laminate material bottom layer;
oscillating, with a laminate oscillating device, each of the first pair of elasticized laminates in the cross-machine direction to impart a curvature to each of the first and second side edges of each of the first pair of elasticized laminates, the oscillation occurring within a single plane;
bonding each of the first pair of elasticized laminates to the stream of connected absorbent assemblies while maintaining the imparted curvature; and
separating the stream of connected absorbent assemblies into individual absorbent articles, each article comprising a front region, a rear region, and a crotch region disposed between the front region and the rear region, wherein the first and second side edges and the elastomeric member of each elasticized laminate of each individual absorbent article extend in a curving manner throughout at least the crotch region of each individual absorbent article,
wherein the folded edge of each of the first pair of elasticized laminates is disposed outboard of a side edge of the stream of connected absorbent assemblies along the entire length of the elasticized laminates.

12. The method of claim 11, further comprising:
moving a second pair of elasticized laminates in the machine direction, each of the second pair of elasticized laminates comprising:
a laminate material having first side edge and a second side edge, at least one of the first side edge and the second side edge being a folded edge, wherein the laminate material comprises a laminate material top layer and a laminate material bottom layer; and
an elastomeric member disposed between the laminate material top layer and the laminate material bottom layer;
oscillating, with a laminate oscillating device, each of the second pair of elasticized laminates in the cross-machine direction to impart a curvature to each of the first and second side edges of each of the second pair of elasticized laminates; and
bonding each of the second pair of elasticized laminates to the stream of connected absorbent assemblies while maintaining the imparted curvature,
wherein the curvature of each of the first pair of elasticized laminates is different than the curvature of each of the second pair of elasticized laminates.

13. The method of claim 12, wherein each of the second pair of elasticized laminates form elasticized containment flaps in the individual absorbent articles.

14. The method of claim 13, wherein each of the second pair of elasticized laminates is bonded to the stream of connected absorbent assemblies along a straight bond line.

15. The method of claim 13, wherein each of the second pair of elasticized laminates is bonded to the stream of connected absorbent assemblies along a curving bond line.

16. The method of claim 12, wherein each of the first pair of elasticized laminates is bonded to the stream of connected absorbent assemblies such that each of the first pair of elasticized laminates covers at least a portion of one of the second pair of elasticized laminates.

17. The method of claim 12, wherein each of the second pair of elasticized laminates are oscillated in the cross-machine direction in opposing directions and wherein each of the second pair of elasticized laminates are bonded to a different portion of the stream of connected absorbent assemblies located on different sides of the central longitudinal axis.

18. The method of claim 11, wherein each of the first pair of elasticized laminates further comprise:
a first group of one or more elastomeric members; and
a second group of one or more elastomeric members spaced from the first group of elastomeric members, and
wherein each of the first pair of elasticized laminates is attached to the stream of connected absorbent assemblies at a location between the first group of one or more elastomeric members, which form elasticized leg cuffs in the individual absorbent articles, and the second group of one or more elastomeric members, which form elasticized containment flaps in the individual absorbent articles.

19. The method of claim 11, wherein each of the first pair of elasticized laminates are oscillated in the cross-machine direction in opposing directions and wherein each of the first pair of elasticized laminates are bonded to different portions of the stream of connected absorbent assemblies located on different sides of the central longitudinal axis.

20. The method of claim 11, wherein the laminate oscillating device comprises a laminate guide having a proximal end and a distal end connected by a first support brace extending along a first side edge of the laminate guide and a second support brace spaced from the first support brace and extending along a second side edge of the laminate guide.

\* \* \* \* \*